United States Patent
Huber et al.

(10) Patent No.: US 11,041,197 B2
(45) Date of Patent: *Jun. 22, 2021

(54) EFFICIENT OPTICAL ANALYSIS OF POLYMERS USING ARRAYS OF NANOSTRUCTURES

(71) Applicant: Quantapore, Inc., South San Francisco, CA (US)

(72) Inventors: Martin Huber, Menlo Park, CA (US); Stuart Davidson, South San Francisco, CA (US)

(73) Assignee: Quantapore, Inc., South San Francisco, CA (US)

(*) Notice: Subject to any disclaimer, the term of this patent is extended or adjusted under 35 U.S.C. 154(b) by 120 days.

This patent is subject to a terminal disclaimer.

(21) Appl. No.: 16/553,040

(22) Filed: Aug. 27, 2019

(65) Prior Publication Data

US 2020/0010886 A1 Jan. 9, 2020

Related U.S. Application Data

(63) Continuation of application No. 15/453,542, filed on Mar. 8, 2017, now abandoned, which is a
(Continued)

(51) Int. Cl.
*C12Q 1/6869* (2018.01)
*G01N 21/64* (2006.01)
(Continued)

(52) U.S. Cl.
CPC ......... *C12Q 1/6869* (2013.01); *C12Q 1/6874* (2013.01); *G01N 21/6428* (2013.01);
(Continued)

(58) Field of Classification Search
None
See application file for complete search history.

(56) References Cited

U.S. PATENT DOCUMENTS

| 4,161,690 A | 7/1979 | Feier |
| 4,962,037 A | 10/1990 | Jett et al. |

(Continued)

FOREIGN PATENT DOCUMENTS

| CN | 1403817 | 3/2003 |
| CN | 201302544 | 9/2009 |

(Continued)

OTHER PUBLICATIONS

US 8,008,014 B2, 08/2011, Gershow et al. (withdrawn)
(Continued)

*Primary Examiner* — Samuel C Woolwine
(74) *Attorney, Agent, or Firm* — Stephen C. Macevicz; Vince M. Powers; Levine Bagade Han LLP

(57) ABSTRACT

The invention is directed to methods and apparatus for detecting sequences of optical signals from parallel reactions on an array of nanostructures, such as nanopores, nanowells, or nanoparticles. In accordance with the invention, an array of nanostructures is provided, each nanostructure comprising a reaction site and each capable of confining a reaction that generates a sequence of optical signals, and the nanostructures of the array being arranged in clusters each comprising a number of nanostructures. Each different cluster is disposed within a different resolution limited area and the number of nanostructures in each cluster is either greater than one or a random variable with an average value greater than zero. Optical signals from reactions in the nanostructures are detected by an optical system operatively associated with the array.

8 Claims, 10 Drawing Sheets

Related U.S. Application Data continuation of application No. 14/922,038, filed on Oct. 23, 2015, now Pat. No. 9,624,537.

(60) Provisional application No. 62/068,599, filed on Oct. 24, 2014.

(51) Int. Cl.
  *G01N 33/487* (2006.01)
  *C12Q 1/6874* (2018.01)
  *G01N 21/76* (2006.01)

(52) U.S. Cl.
  CPC ... *G01N 21/6452* (2013.01); *G01N 33/48721* (2013.01); *G01N 21/648* (2013.01); *G01N 21/76* (2013.01); *G01N 2021/6439* (2013.01); *G01N 2201/06113* (2013.01)

(56) References Cited

U.S. PATENT DOCUMENTS

| | | |
|---|---|---|
| 5,131,755 A | 7/1992 | Chadwick et al. |
| 5,356,776 A | 10/1994 | Kambara et al. |
| 5,387,926 A | 2/1995 | Bellan |
| 5,405,747 A | 4/1995 | Jett et al. |
| 5,470,705 A | 11/1995 | Grossman et al. |
| 5,580,732 A | 12/1996 | Grossman et al. |
| 5,624,800 A | 4/1997 | Grossman et al. |
| 5,795,782 A | 8/1998 | Church et al. |
| 5,798,042 A | 8/1998 | Chu et al. |
| 5,821,058 A | 10/1998 | Smith et al. |
| 5,945,312 A | 8/1999 | Goodman et al. |
| 5,989,871 A | 11/1999 | Grossman et al. |
| 6,015,714 A | 1/2000 | Baldarelli et al. |
| 6,083,763 A | 7/2000 | Balch |
| 6,136,543 A | 10/2000 | Anazawa et al. |
| 6,210,896 B1 | 4/2001 | Chan |
| 6,211,955 B1 | 4/2001 | Basiji et al. |
| 6,249,341 B1 | 6/2001 | Basiji et al. |
| 6,251,303 B1 | 6/2001 | Bawendi et al. |
| 6,252,303 B1 | 6/2001 | Huang |
| 6,263,286 B1 | 7/2001 | Gilmanshin et al. |
| 6,267,872 B1 | 7/2001 | Akeson et al. |
| 6,325,968 B1 | 12/2001 | Fricker et al. |
| 6,335,420 B1 | 1/2002 | Bruening et al. |
| 6,335,440 B1 | 1/2002 | Lee et al. |
| 6,355,420 B1 | 3/2002 | Chan |
| 6,362,002 B1 | 3/2002 | Denison et al. |
| 6,413,792 B1 | 7/2002 | Sauer et al. |
| 6,426,231 B1 | 7/2002 | Bayley et al. |
| 6,428,959 B1 | 8/2002 | Deamer |
| 6,429,897 B2 | 8/2002 | Derndinger et al. |
| 6,447,724 B1 | 9/2002 | Jensen et al. |
| 6,464,842 B1 | 10/2002 | Golovchenko et al. |
| 6,465,193 B2 | 10/2002 | Akeson et al. |
| 6,473,176 B2 | 10/2002 | Basiji et al. |
| 6,498,010 B1 | 12/2002 | Fitzgerald et al. |
| 6,503,757 B1 | 1/2003 | Chow |
| 6,504,943 B1 | 1/2003 | Sweatt et al. |
| 6,511,802 B1 | 1/2003 | Albrecht et al. |
| 6,528,258 B1 | 3/2003 | Russell |
| 6,537,755 B1 | 3/2003 | Drmanac |
| 6,583,865 B2 | 6/2003 | Basiji et al. |
| 6,608,680 B2 | 8/2003 | Basiji et al. |
| 6,608,682 B2 | 8/2003 | Ortyn et al. |
| 6,616,895 B2 | 9/2003 | Dugas et al. |
| 6,617,113 B2 | 9/2003 | Deamer |
| 6,618,140 B2 | 9/2003 | Frost et al. |
| 6,618,679 B2 | 9/2003 | Loehrlein et al. |
| 6,627,067 B1 | 9/2003 | Branton et al. |
| 6,671,044 B2 | 12/2003 | Ortyn et al. |
| 6,673,615 B2 | 1/2004 | Denison et al. |
| 6,706,203 B2 | 3/2004 | Barth et al. |
| 6,723,515 B2 | 4/2004 | Barron |
| 6,743,905 B2 | 6/2004 | Woo et al. |
| 6,746,594 B2 | 6/2004 | Akeson et al. |
| 6,752,914 B1 | 6/2004 | Hassard |
| 6,756,204 B2 | 6/2004 | Grossman et al. |
| 6,758,961 B1 | 7/2004 | Vogel et al. |
| 6,772,070 B2 | 8/2004 | Gilmanshin et al. |
| 6,790,671 B1 | 9/2004 | Austin et al. |
| 6,821,726 B1 | 11/2004 | Dahm et al. |
| 6,824,659 B2 | 11/2004 | Bayley et al. |
| 6,830,670 B1 | 12/2004 | Viovy et al. |
| 6,855,551 B2 | 2/2005 | Bawendi et al. |
| 6,856,390 B2 | 2/2005 | Nordman et al. |
| 6,906,749 B1 | 6/2005 | Fox |
| 6,916,665 B2 | 7/2005 | Bayley et al. |
| 6,936,433 B2 | 8/2005 | Akeson et al. |
| 6,947,128 B2 | 9/2005 | Basiji et al. |
| 6,952,651 B2 | 10/2005 | Su |
| 6,975,400 B2 | 12/2005 | Ortyn et al. |
| 6,982,146 B1 | 1/2006 | Schneider et al. |
| 6,998,251 B2 | 2/2006 | Guttman et al. |
| 7,001,792 B2 | 2/2006 | Sauer et al. |
| 7,005,264 B2 | 2/2006 | Su et al. |
| 7,008,547 B2 | 3/2006 | Chen et al. |
| 7,049,104 B2 | 5/2006 | Kambara et al. |
| 7,052,847 B2 | 5/2006 | Korlach et al. |
| 7,056,661 B2 | 6/2006 | Korlach et al. |
| 7,056,676 B2 | 6/2006 | Korlach et al. |
| 7,060,507 B2 | 6/2006 | Akeson et al. |
| 7,074,569 B2 | 7/2006 | Woo et al. |
| 7,129,050 B2 | 10/2006 | Grossman et al. |
| 7,189,503 B2 | 3/2007 | Akeson et al. |
| 7,201,836 B2 | 4/2007 | Vogel et al. |
| 7,235,184 B2 | 6/2007 | Dugas et al. |
| 7,235,361 B2 | 6/2007 | Bawendi et al. |
| 7,238,485 B2 | 7/2007 | Akeson et al. |
| 7,244,349 B2 | 7/2007 | Vogel et al. |
| 7,248,771 B2 | 7/2007 | Schmidt et al. |
| 7,250,115 B2 | 7/2007 | Barth |
| 7,271,896 B2 | 9/2007 | Chan et al. |
| 7,279,337 B2 | 10/2007 | Zhu |
| 7,280,207 B2 | 10/2007 | Oldham et al. |
| 7,285,010 B2 | 10/2007 | Hatakeyama et al. |
| 7,364,851 B2 | 4/2008 | Berlin et al. |
| 7,371,533 B2 | 5/2008 | Slater et al. |
| 7,381,315 B2 | 6/2008 | Grossman et al. |
| 7,387,715 B2 | 6/2008 | Vogel et al. |
| 7,390,457 B2 | 6/2008 | Schembri |
| 7,397,232 B2 | 7/2008 | Hu et al. |
| 7,410,564 B2 | 8/2008 | Flory |
| 7,428,047 B2 | 9/2008 | Oldham et al. |
| 7,438,193 B2 | 10/2008 | Yang et al. |
| 7,444,053 B2 | 10/2008 | Schmidt et al. |
| 7,468,271 B2 | 12/2008 | Golovchenko et al. |
| 7,476,503 B2 | 1/2009 | Turner et al. |
| 7,553,730 B2 | 6/2009 | Barth et al. |
| 7,567,695 B2 | 7/2009 | Frost et al. |
| 7,595,023 B2 | 9/2009 | Lewis et al. |
| 7,609,309 B2 | 10/2009 | Brown et al. |
| 7,622,934 B2 | 11/2009 | Hibbs et al. |
| 7,625,706 B2 | 12/2009 | Akeson et al. |
| 7,651,599 B2 | 1/2010 | Blaga et al. |
| 7,666,593 B2 | 2/2010 | Lapidus |
| 7,670,770 B2 | 3/2010 | Chou et al. |
| 7,678,562 B2 | 3/2010 | Ling |
| 7,744,816 B2 | 6/2010 | Su et al. |
| 7,777,505 B2 | 8/2010 | White et al. |
| 7,803,607 B2 | 9/2010 | Branton et al. |
| 7,835,870 B2 | 11/2010 | Nair et al. |
| 7,838,873 B2 | 11/2010 | Clevenger et al. |
| 7,843,562 B2 | 11/2010 | Chan et al. |
| 7,846,738 B2 | 12/2010 | Golovchenko et al. |
| 7,849,581 B2 | 12/2010 | White et al. |
| 7,871,777 B2 | 1/2011 | Schneider et al. |
| 7,883,869 B2 | 2/2011 | Ju et al. |
| 7,897,338 B2 | 3/2011 | Woo et al. |
| 7,947,454 B2 | 5/2011 | Akeson et al. |
| 7,972,858 B2 | 7/2011 | Meller et al. |
| 8,105,846 B2 | 1/2012 | Bayley et al. |
| 8,206,568 B2 | 6/2012 | Branton et al. |
| 8,394,584 B2 | 3/2013 | Timp et al. |

(56) References Cited

U.S. PATENT DOCUMENTS

| | | |
|---|---|---|
| 8,394,640 B2 | 3/2013 | Golovchenko et al. |
| 8,435,775 B2 | 5/2013 | Holliger et al. |
| 8,440,403 B2 | 5/2013 | Frayling |
| 8,771,491 B2 | 7/2014 | Huber |
| 8,802,838 B2 | 8/2014 | Meller et al. |
| 8,865,078 B2 | 10/2014 | Chiou et al. |
| 8,865,455 B2 | 10/2014 | Frayling |
| 9,121,843 B2 | 9/2015 | Meller et al. |
| 2002/0034762 A1 | 3/2002 | Muller et al. |
| 2002/0119455 A1 | 8/2002 | Chan |
| 2003/0003463 A1 | 1/2003 | Rothberg et al. |
| 2003/0064366 A1 | 4/2003 | Hardin et al. |
| 2003/0092005 A1 | 5/2003 | Levene et al. |
| 2003/0096220 A1 | 5/2003 | Lafferty et al. |
| 2003/0143614 A1 | 7/2003 | Drmanac |
| 2003/0148544 A1 | 8/2003 | Nie et al. |
| 2003/0174992 A1 | 9/2003 | Levene et al. |
| 2003/0207326 A1 | 11/2003 | Su et al. |
| 2003/0215881 A1 | 11/2003 | Bayley et al. |
| 2004/0002089 A1 | 1/2004 | Dubertret et al. |
| 2004/0033492 A1 | 2/2004 | Chen |
| 2004/0137158 A1 | 7/2004 | Kools et al. |
| 2004/0146430 A1 | 7/2004 | Dugas |
| 2004/0175710 A1 | 9/2004 | Haushalter |
| 2004/0214221 A1 | 10/2004 | Muehlegger et al. |
| 2005/0014154 A1 | 1/2005 | Weizenegger |
| 2005/0019784 A1 | 1/2005 | Su et al. |
| 2005/0095599 A1 | 5/2005 | Pittaro et al. |
| 2005/0130159 A1 | 6/2005 | Rigler et al. |
| 2005/0130173 A1 | 6/2005 | Leamon et al. |
| 2005/0136408 A1 | 6/2005 | Tom et al. |
| 2005/0147992 A1 | 7/2005 | Quake et al. |
| 2005/0153284 A1 | 7/2005 | Foldes et al. |
| 2005/0164211 A1 | 7/2005 | Hannah |
| 2005/0186576 A1 | 8/2005 | Chan et al. |
| 2005/0186629 A1 | 8/2005 | Barth |
| 2005/0196876 A1 | 9/2005 | Chan et al. |
| 2005/0227239 A1 | 10/2005 | Joyce |
| 2005/0241933 A1 | 11/2005 | Branton et al. |
| 2005/0282229 A1 | 12/2005 | Su et al. |
| 2006/0003458 A1 | 1/2006 | Golovchenko et al. |
| 2006/0019247 A1 | 1/2006 | Su et al. |
| 2006/0019259 A1 | 1/2006 | Joyce |
| 2006/0063171 A1 | 3/2006 | Akeson et al. |
| 2006/0147942 A1 | 7/2006 | Buzby |
| 2006/0210995 A1 | 9/2006 | Joyce |
| 2006/0231419 A1 | 10/2006 | Barth et al. |
| 2006/0251371 A1 | 11/2006 | Schmidt et al. |
| 2006/0292041 A1 | 12/2006 | Dugas et al. |
| 2007/0012865 A1 | 1/2007 | Katzir et al. |
| 2007/0037199 A1 | 2/2007 | Takahashi et al. |
| 2007/0042366 A1 | 2/2007 | Ling |
| 2007/0054276 A1 | 3/2007 | Sampson |
| 2007/0172858 A1 | 7/2007 | Hardin et al. |
| 2007/0172865 A1 | 7/2007 | Hardin et al. |
| 2007/0190542 A1 | 8/2007 | Ling et al. |
| 2007/0190543 A1 | 8/2007 | Livak |
| 2007/0202008 A1 | 8/2007 | Schembri et al. |
| 2007/0215472 A1 | 9/2007 | Slater et al. |
| 2007/0218494 A1 | 9/2007 | Slater et al. |
| 2007/0224613 A1 | 9/2007 | Strathmann |
| 2007/0231795 A1 | 10/2007 | Su |
| 2007/0264623 A1 | 11/2007 | Wang et al. |
| 2008/0025875 A1 | 1/2008 | Martin et al. |
| 2008/0032290 A1 | 2/2008 | Young |
| 2008/0050752 A1 | 2/2008 | Sun et al. |
| 2008/0187915 A1 | 8/2008 | Polonsky et al. |
| 2008/0193956 A1 | 8/2008 | Kricka et al. |
| 2008/0218184 A1 | 9/2008 | White et al. |
| 2008/0254995 A1 | 10/2008 | Kim et al. |
| 2008/0261204 A1 | 10/2008 | Lexow |
| 2008/0274905 A1 | 11/2008 | Greene |
| 2008/0311375 A1 | 12/2008 | Harnack et al. |
| 2009/0021735 A1 | 1/2009 | Oldham et al. |
| 2009/0024331 A1 | 1/2009 | Tomaney et al. |
| 2009/0029477 A1 | 1/2009 | Meller et al. |
| 2009/0035777 A1 | 2/2009 | Kokoris et al. |
| 2009/0061447 A1 | 3/2009 | Schneider |
| 2009/0066315 A1 | 3/2009 | Hu et al. |
| 2009/0136958 A1 | 5/2009 | Gershow et al. |
| 2009/0137007 A1 | 5/2009 | Korlach et al. |
| 2009/0148348 A1 | 6/2009 | Pettigrew et al. |
| 2009/0185955 A1 | 7/2009 | Nellissen |
| 2009/0222216 A1 | 9/2009 | Hibbs et al. |
| 2009/0250615 A1 | 10/2009 | Oldham et al. |
| 2009/0277869 A1 | 11/2009 | Dugas |
| 2009/0298075 A1 | 12/2009 | Travers et al. |
| 2009/0305278 A1 | 12/2009 | Hardin et al. |
| 2009/0314939 A1 | 12/2009 | Stern et al. |
| 2010/0025249 A1 | 2/2010 | Polonsky et al. |
| 2010/0029508 A1 | 2/2010 | Austin et al. |
| 2010/0035260 A1 | 2/2010 | Olasagasti et al. |
| 2010/0035268 A1 | 2/2010 | Beechem et al. |
| 2010/0075309 A1 | 3/2010 | Maxham et al. |
| 2010/0103416 A1 | 4/2010 | Oldham et al. |
| 2010/0227913 A1 | 9/2010 | Lyakhov et al. |
| 2010/0262379 A1 | 10/2010 | Frazier |
| 2010/0292101 A1 | 11/2010 | So |
| 2010/0331194 A1 | 12/2010 | Turner et al. |
| 2011/0053284 A1 | 3/2011 | Meller et al. |
| 2011/0172404 A1 | 7/2011 | Luo et al. |
| 2011/0177498 A1 | 7/2011 | Clarke et al. |
| 2011/0177978 A1 | 7/2011 | Luo et al. |
| 2011/0257043 A1 | 10/2011 | Meller et al. |
| 2011/0308950 A1 | 12/2011 | Sakai et al. |
| 2012/0055792 A1 | 3/2012 | Gundlach et al. |
| 2012/0135410 A1 | 5/2012 | Soni et al. |
| 2012/0199482 A1 | 8/2012 | Meller et al. |
| 2012/0261261 A1 | 10/2012 | Huber |
| 2013/0040827 A1 | 2/2013 | Macevicz |
| 2013/0146456 A1 | 6/2013 | Gundlach et al. |
| 2013/0176563 A1 | 7/2013 | Ozawa et al. |
| 2013/0203050 A1 | 8/2013 | Huber et al. |
| 2013/0203610 A1 | 8/2013 | Meller et al. |
| 2013/0256118 A1 | 10/2013 | Meller et al. |
| 2014/0087474 A1 | 3/2014 | Huber |
| 2014/0255935 A1 | 9/2014 | Huber |
| 2014/0367259 A1 | 12/2014 | Frayling et al. |
| 2015/0204840 A1 | 7/2015 | Soares et al. |
| 2017/0175186 A1 | 6/2017 | Huber et al. |

FOREIGN PATENT DOCUMENTS

| | | |
|---|---|---|
| EP | 1682673 | 7/2006 |
| WO | WO 2001/018247 | 3/2001 |
| WO | WO 2005/045392 | 5/2005 |
| WO | WO 2006/052882 | 5/2006 |
| WO | WO 2008/049795 | 5/2008 |
| WO | WO 2008/092760 | 8/2008 |
| WO | WO 2009/007743 | 1/2009 |
| WO | WO 2009/020682 | 2/2009 |
| WO | WO 2009/056831 | 5/2009 |
| WO | WO 2009/092035 | 7/2009 |
| WO | WO 2010/002883 | 1/2010 |
| WO | WO 2010/007537 | 1/2010 |
| WO | WO 2010/116595 | 10/2010 |
| WO | WO 2011/040996 | 4/2011 |
| WO | WO 2011/050147 | 4/2011 |
| WO | WO 2011/067559 | 6/2011 |
| WO | WO 2012/121756 | 9/2012 |
| WO | WO 2012/170499 | 12/2012 |
| WO | WO 2014/066902 | 5/2014 |
| WO | WO 2014/066905 | 5/2014 |
| WO | WO 2014/122654 | 8/2014 |
| WO | WO 2014/190322 | 11/2014 |

OTHER PUBLICATIONS

Aksimentiev, A. et al., "Microscopic Kinetics of DNA Translocation through Synthetic Nanopores," *Biophysical Journal*, vol. 87, pp. 2086-2097, Sep. 2004.

(56) References Cited

OTHER PUBLICATIONS

Algar, W. R. et al. "Quantum dots as donors in fluorescence resonance energy transfer for the bioanalysis of nucleic acids, proteins, and other biological molecules," *Anal Bioanal Chem*, vol. 391, pp. 1609-1618, Jul. 2008.
Anderson, B.N. et al. "Probing Solid-State Nanopores with Light for the Detection of Unlabeled Analytes," *ACS Nano*, 8(11), pp. 11836-11845, Nov. 2014.
Anderson, J. et al. "Incorporation of reporter-labeled nucleotides by DNA polymerases," *Biotechniques*, 38(2): 257-263, Feb. 2005.
Anderson, M. et al, "Next Generation DNA Sequencing and the Future of Genomic Medicine," *Genes*, vol. 1, pp. 38-69, Jun. 2010.
Augustin, M.A. et al. "Progress towards single-molecule sequencing: enzymatic synthesis of nucleotide-specifically labeled DNA," *Journal of Biotechnology*, 86(3), pp. 289-301, Apr. 2001.
Australian Patent Application No. 2010301128 filed May 13, 2010 in the name of Huber, Office Action dated Aug. 15, 2014.
Baker, L.A. et al., "A makeover for membranes," *Nature Nanotechnology*, vol. 3, pp. 73-74, Feb. 2008.
Bayley, H., "Sequencing single molecules of DNA," *Current Opinion in Chemical Biology*,10(6), pp. 628-637, Dec. 2006.
Begovich, A.B. et al., "A Missense Single-Nucleotide Polymorphism in a Gene Encoding a Protein Tyrosine Phosphatase (PTPN22) Is Associated with Rheumatoid Arthritis," *The American Journal of Human Genetics*, vol. 75, No. 2, pp. 330-337, Aug. 1, 2004.
Brakmann, S. "High-Density Labeling of DNA for Single Molecule Sequencing," *Methods in Molecular Biology*, vol. 283, pp. 137-144, Jun. 2004.
Brakmann, S. et al. "High-Density Labeling of DNA: Preparation and Characterization of the Target Material for Single-Molecule Sequencing," *Angew. Chem. Int. Ed.*, 40(8), pp. 1427-1429, Apr. 2001.
Branton, D. et al, "The potential and challenges of nanopore sequencing," *Nature Biotechnology*, 26(10), pp. 1146-1153, Oct. 2008.
Butler, T. Z. et al., "Single-molecule DNA detection with an engineered MspA protein nanopore," *Proceedings of the National Academy of Sciences*, 105(52), pp. 20647-20652, Dec. 30, 2008.
Chan, E. Y. et al. "DNA Mapping Using Microfluidic Stretching and Single-Molecule Detection of Fluorescent Site-Specific Tags," *Genome Research*, vol. 14, pp. 1137-1146, 2004.
Chan, W.C. et al. "Quantum Dot Bioconjugates for Ultrasensitive Nonisotopic Detection," *Science*, vol. 281, pp. 2016-2018, Sep. 25, 1998.
Chansin, et al. "Single-Molecule Spectroscopy Using Nanoporous Membranes," *Nano Letters*,vol. 7, No. 9; pp. 2901-2906, Aug. 25, 2007.
Chen, P. et al, "Atomic Layer Deposition to Fine-Tune the Surface Properties and Diameters of Fabricated Nanopores," *Nano Letters*, 4(7), pp. 1333-1337, Jun. 25, 2004.
Cherf, G. et al, "Automated forward and reverse ratcheting of DNA in a nanopore at 5-A precision," *Nat Biotechnol.*, 30(4), 6 pages, Feb. 14, 2012.
Clarke, J. et al, "Continuous base identification for single-molecule nanopore DNA sequencing," *Nature Nanotechnology*, 4(4), pp. 265-270, Apr. 2009.
Danelon, C. et al. "Fabrication and Functionalization of Nanochannels by Electron-Beam-Induced Silicon Oxide Deposition," *Langmuir*, vol. 22, pp. 10711-10715, Sep. 6, 2006.
Deamer, et al., "Characterization of Nucleic Acids by Nanopore Analysis," *Acc. Chem. Res.*, 35(10), pp. 817-825, 2002.
Deamer, et al., "Nanopores and nucleic acids: prospects for ultrarapid sequencing," *Trends in Biotechnology*,18(4), abstract only (2 pages), Apr. 1, 2000.
Deblois, R. et al, "Counting and Sizing of Submicron Particles by the Resistive Pulse Technique," *Rev. Sci. Instruments*, 41(7), pp. 909-916, Jul. 1970.
Dekker, C. "Solid-state nanopores," *Nature Nanotechnology*, vol. 2, pp. 209-215, Apr. 2007.

Dela Torre, R. et al. "Fabrication and Characterization of Solid-state Nanopore Arrays for High Throughput DNA Sequencing," *Nanotechnology*,23(38), 12 pages, Sep. 28, 2012.
Dennis, A.M. et al., "Quantum Dot—Fluorescent Protein Pairs as Novel Fluorescence Resonance Energy Transfer Probes," *Nano Lett.*, vol. 8, No. 5, pp. 1439-1445, Apr. 16, 2008, American Chemical Society.
Dorre, K. et al. "Highly efficient single molecule detection in microstructures," *Journal of Biotechnology*, 86(3), pp. 225-236, Apr. 2001.
EID et al, "Real-time DNA sequencing from single polymerase molecules," *Science*, 323: 133-138, Supplemental Material, Jan. 2, 2009.
Eigen, M. et al. "Sorting single molecules: Application to diagnostics and evolutionary biotechnology," *Proc. Natl. Acad. Sci.*, vol. 91, pp. 5740-5747, Jun. 1994.
Etoh, et al. "An Image Sensor Which Captures 100 Consecutive Frames at 1000000 Frames/s," *IEEE Transactions on Electron Devices*, vol. 50. No. 1; pp. 144-151, Jan. 2003.
European Patent Application No. 10820963.6 filed May 13, 2010 in the name of Huber, Search Report and Opinion dated Dec. 20, 2013.
Foldes-Papp, Z. et al. "Fluorescent high-density labeling of DNA: error-free substitution for a normal nucleotide," *Journal of Biotechnology*, 86(3), pp. 237-253, Mar. 2001.
Fologea, et al. "Detecting Single Stranded DNA with a Solid State Nanopore," *Nano Letters*, 5 (10), abstract only, Aug. 31, 2005.
Fontes, A. et al. "Quantum Dots in Biomedical Research," Biomedical Engineering—Technical Applications in Medicine, Chapter 12, pp. 269-290, Sep. 6, 2012.
Freeman, J. et al, "Profiling the T-cell receptor beta-chain repertoire by massively parallel sequencing," Genome Research, vol. 19, pp. 1817-1824, Jun. 2009.
Galla et al. "Microfluidic carbon-blackened polydimethylsiloxane device with reduced ultra violet 1-4 background fluorescence for simultaneous two-color ultra violetivisible-laser induced fluorescence detection in single cell analysis," *Biomicrofluidics* 6, pp. 014104-1 to 014104-10, Jan. 12, 2012.
Gierlich, J. et al, "Synthesis of Highly Modified DNA by a Combination of PCR with Alkyne-Bearing Triphosphates and Click Chemistry," *Chem. Eur. J.*, vol. 13, pp. 9486-9494, Nov. 16, 2007.
Giller, G. et al. "Incorporation of reporter molecule-labeled nucleotides by DNA polymerases. I. Chemical synthesis of various reporter group—labeled 2'-deoxyribonucleoside-5'-triphosphates," *Nucleic Acids Research*, 31(10), pp. 2630-2635, May 2003.
Grayson, A. et al, " A BioMEMS Review: MEMS Technology for Physiologically Integrated Devices," *Proceedings IEEE*, 92(1), pp. 6-21, Jan. 2004.
Gu, L. et al, "Single molecule sensing by nanopores and nanopore devices," *Analyst*,135(3), pp. 441-451, 2010.
Gupta, et al., "Single-molecule DNA sequencing technologies for future genomic research," *Trends in Biotechnology*, 26(11), pp. 602-611, Nov. 1, 2008.
Ha, T. et al., "Probing the interaction between two single molecules: fluorescence resonance energy transfer between a single donor and a single acceptor," *Proc. Natl. Acad. Sci USA*, vol. 93, No. 13, pp. 6264-6268, Jun. 25, 1996.
Hall, A. R. et al. "Hybrid pore formation by directed insertion of alpha hemolysin into solid-state nanopores," *Nature Nanotechnology*, 5(12), pp. 874-877, Dec. 2010.
He, H. et al., "Single Nonblinking CdTe Quantum Dots Synthesized in Aqueous Thiopropionic Acid," *Angew. Chem. Int. Ed*. vol. 45, pp. 7588-7591, Oct. 2006.
Heins, E.A. et al., "Detecting Single Porphyrin Molecules in a Conically Shaped Synthetic Nanopore," *Nano Letters*, 5(9), pp. 1824-1829, Jul. 26, 2005.
Heins, E.A. et al., "Detecting Single Porphyrin Molecules in a Conically Shaped Synthetic Nanopore," *Nano Letters*, 5(9), pp. 1824-1829, Supporting Information, Jul. 26, 2005.
Heintzmann, R. et al., "Breaking the resolution limit in light microscopy," *Briefings in Functional Genomics and Proteomics*, 5(4), pp. 289-301, Dec. 2006.
Hemminger, "Visualizing and Understanding Complex MicrolNanonuidic Flow Behavior," Dissertation, The Ohio State

(56) References Cited

OTHER PUBLICATIONS

University, 2010, available online at <http://etd.ohiolink.edulsend•pdf. cgUHemminger%200rin%20L.pdf?osu1275398565>.
Henriquez, R. et al, "The resurgence of Coulter counting for analyzing nanoscale objects," *The Analyst*, 129, pp. 478-482, 2004.
Hlawacek, G. "Helium Ion Microscopy," *Journal of Vacuum Sciences B*, 32:020801, 16 pages, Feb. 6, 2014.
Hoevel, T. et al., "Cisplatin-Digoxigenin mRNA labeling for non-radioactive detection of mRNA hybridized onto nucleic acid cDNA arrays," *Biotechniques*, vol. 27, No. 5, pp. 1064-1067, Nov. 1999.
Holt, R. et al, "The new paradigm of flow cell sequencing," *Genome Research*, vol. 18, pp. 839-846, Jun. 2008.
Hsieh et al. "Effective Enhancement of Fluorescence Detection Efficiency In Protein MIcroarrayAssays: Application of a Highly AuorInated Organosllane as the Blocking Agent on the Background Surface by a Facile Vapor-Phase Deposition Process," *Anal. Chem.*, 88:7908-7916, Aug. 25, 2009.
Huang, S. et al. "High-throughput optical sensing of nucleic acids in a nanopore array," *Nature Nanotechnology*, vol. 10, pp. 986-991, Aug. 2015.
Iqbal, S. M. et al., "Solid-state nanopore channels with DNA selectivity," *Nature Nanotechnology*, pp. 1-6, Apr. 1, 2007.
Ito, T. et al., "Observation of DNA transport through a single carbon nanotube channel using fluorescence microscopy," *Chem. Commun*, vol. 12, pp. 1482-1483, Aug. 2003.
Ivankin, A. et al. "Label-Free Optical Detection of Biomolecular Translocation through Nanopore Arrays," *ACS Nano*, 8(10), pp. 10774-10781, Sep. 2014.
Jagtiani, A. et al, "A label-free high throughput resistive-pulse sensor for simultaneous differentiation and measurement of multiple particle-laden analytes," *J. Micromech. Microeng.*, 16, pp. 1530-1539, Jun. 26, 2006.
Japanese Patent Application No. 2012-532069 filed May 13, 2010 in the name of Huber, Final Office Action dated Apr. 17, 2015.
Japanese Patent Application No. 2012-532069 filed May 13, 2010 in the name of Huber, Office Action dated Aug. 1, 2014.
Japanese Patent Application No. 2014-224165 filed May 13, 2010 in the name of Huber, Office Action dated Oct. 15, 2015.
Johansson, MK et al. "Choosing Reporter-Quencher Pairs for Efficient Quenching Through Formation of Intramolecular Dimers," *Methods in Molecular Biology*, vol. 335:2, pp. 17-29, 2006.
Johansson, MK et al. "Intramolecular Dimers: A New Design Strategy for Fluorescence-Quenched Probes," *Chem. Eur. J.*, 9, 3466-3471, Jul. 2003.
Kang, X. et al., "A storable encapsulated bilayer chip containing a single protein nanopore," *J Am Chem Soc.* vol. 129, No. 15, pp. 4701-4705, Mar. 22, 2007.
Kasianowicz, J.J. et al., "Characterization of Individual Polynucleotide Molecules Using a Membrane Channel," *Proc. Natl. Acad. Sci USA*, vol. 93, pp. 13770-13773, Nov. 1996.
Keyser, U. F. "Controlling molecular transport through nanopores," *Journal of the Royal Society Interface*,10 page, Oct. 7, 2011.
Kircher, M. et al, "High-throughput DNA sequencing-concepts and limitations," *Bioessays*, vol. 32, pp. 524-536, Jun. 2010.
Kleefen, A. et al. "Multiplexed Parallel Single Transport Recordings on Nanopore Arrays," *Nano Letters*, vol. 10, pp. 5080-5087, Oct. 27, 2010.
Kocer, A. et al. "Nanopore sensors: From hybrid to abiotic systems," *Biosensors and Bioelectronics*, vol. 38, 10 pages, Jun. 2012.
Kolb, H. et al, "Click Chemistry: Diverse Chemical Function from a Few Good Reactions," *Angew. Chem. Int. Ed.*, vol. 40, pp. 2005-2021, Jun. 1, 2001.
Kristensen, V. N. et al., "High-Throughput Methods for Detection of Genetic Variation," *BioTechniques*, 30(2), pp. 318-332, Feb. 2001.
Lee et al. "High aspect ratio polymer microstructures and cantilevers for bIoMEMS using low energy ion beam and photolithography," *Sensors and Actuators A*, 71:144-149, Apr. 1998.
Lerner, H. et al, "Prospects for the Use of Next-Generation Sequencing Methods in Ornithology," *The Auk*, 127(1), pp. 4-15, Feb. 2010.

Levene et al, "Zero mode waveguide for single-molecule analysis in high concentration," *Science*, 299: 682-686, Jan. 31, 2003.
Li et al., "DNA Molecules and Configurations in a Solid-State Nanopore Microscope," *Nat. Mater*, vol. 2, pp. 611-615, Sep. 2003.
Li, J. et al., "Nanoscale Ion Beam Sculpting," *Nature*, vol. 412, pp. 166-169, Jul. 12, 2001.
Lin, B. et al., "Recent Patents and Advances in the Next-Generation Sequencing Technologies," *Recent Patents on Biomedical Engineering*, vol. 1, No. 1, pp. 60-67, 2008, Benthan Science Publishers Ltd.
Lo, C.J. et al., "Fabrication of symmetric sub-5 nm nanopores using focused ion and electron beams," *Nanotechnology*, vol. 17, No. 13, pp. 3264-3267, Jul. 2006.
Lu et al. "Parylene Background Fluorescence Study for Biomems Applications," *Transducers*, pp. 176-179, Jun. 21-25, 2009.
Luan et al., "Slowing and controlling the translocation of DNA in a solid-state nanopore," *Nanoscale*, 4(4): 1068-1077, Feb. 21, 2012.
Maitra, R. D. et al. "Recent advances in nanopore sequencing," *Electrophoresis*, vol. 33, pp. 3418-3428, Dec. 2012.
Manrao, E. et al. "Reading DNA at single-nucleotide resolution with a mutant MspA nanopore and phi29 DNA polymerase," *Nat Biotechnol*, 30(4), 6 pages, Mar. 25, 2012.
Marras, S. "Interactive Fluorophore and Quencher Pairs for Labeling Fluorescent Nucleic Acid Hybridization Probes," *Mol Biotechnol*, vol. 38, 247-255, Mar. 2008.
Marras, S. "Selection of Fluorophore and Quencher Pairs for Fluorescent Nucleic Acid Hybridization Probes," *Methods in Molecular Biology*, vol. 335, 3-16, 2006.
McNally, et al. "Optical recognition of converted DNA nucleotides for single•molecule DNA sequencing using nanopore arrays," *Nano Letters*, vol. 10, No. 6; pp. 2237-2244, Jun. 9, 2010.
Meagher, R. J. et al. "Free-solution electrophoresis of DNA modified with drag-tags at both ends," *Electrophoresis*,vol. 27, pp. 1702-1712, May 2006.
Meagher, R. J. et al. "Sequencing of DNA by Free-Solution Capillary Electrophoresis Using a Genetically Engineered Protein Polymer Drag-Tag," *Anal. Chem.*, vol. 80, pp. 2842-2848, Apr. 15, 2008.
Medintz, I.L. et al. "A fluorescence resonance energy transfer-derived structure of a quantum dot-protein bioconjugate nonassembly," *PNAS*, 101(26), pp. 9612-9617, Jun. 29, 2004.
Medintz, I.L. et al. "Quantum dot bioconjugates for imaging, labelling and sensing," *Nature Materials*, vol. 4, 435-446, Jun. 2005.
Meller, A. et al., "Rapid nanopore discrimination between single polynucleotide molecules," *The National Academy of Sciences*, 7 pages, Feb. 1, 2000.
Meller, A. et al., "Voltage-Driven DNA Translocations through a Nanopore," *Phys. Rev. Lett.* 86(15), pp. 3435-3438, Apr. 2001.
Meller, et al., "Single Molecule Measurements of DNA Transport through a Nanopore," *Electrophoresis*, vol. 23, pp. 2583-2591, Aug. 2002.
Metzker, M. "Sequencing technologies—The next generation," *Nature Review Genetics*, vol. 11, pp. 31-46, Jan. 2010.
Meyers, R. "Molecular Biology and Biotechnology, A Comprehensive Desk Reference," VCH Publisher, Inc., New York, NY, pp. 317-319, 1995.
Mir, K., "Ultrasensitive RNA profiling: Counting single molecules on microarrays," *Genome Research*,16:1195-1197, Oct. 2006.
Moerner, W.E. et al. "Methods of single-molecule fluorescence spectroscopy and microscopy," *Review of Scientific Instruments*, 74(8), pp. 3597-3619, Aug. 2003.
Nakane, J. et al, "Evaluation of nanopores as candidates for electronic analyte dectection," *Electrophoresis*, vol. 23, pp. 2592-2601, Aug. 20, 2002.
Nakane, J. et al, "Nanopore sensors for nucleic acid analysis," *J. Phys. Condens. Matter*, Matter 15, pp. R1365-R1393, Aug. 1, 2003.
Ogura, Y. et al., "A Frameshift Mutation in NOD2 Associated with Susceptibility to Crohn's Disease," *Nature*, vol. 411, pp. 603-606, May 31, 2001, Macmillan Magazine Ltd.
Paul, N. et al."PCR incorporation of modified dNTPs: the substrate properties of biotinylated dNTPs," *Biotechniques*, 48(4), 333-334, Apr. 2010.

(56) References Cited

OTHER PUBLICATIONS

PCT International Patent Application No. PCT/US2010/034809 filed May 13, 2010 in the name of Quantapore, Inc., International Search Report and Written Opinion dated Feb. 6, 2014.
PCT International Patent Application No. PCT/US2010/034809 filed May 13, 2010 in the name of Quantapore, Inc., International Search Report and Written Opinion dated Sep. 13, 2010.
PCT International Patent Application No. PCT/US2011/54365 filed Sep. 30, 2011 in the name of Quantapore, Inc., International Search Report and Written Opinion dated Apr. 25, 2012.
PCT International Patent Application No. PCT/US2013/067126 filed Oct. 28, 2013 in the name of Quantapore, Inc., International Search Report and Written Opinion dated May 6, 2014.
PCT International Patent Application No. PCT/US2014/039444 filed May 23, 2014 in the name of Quantapore, Inc., International Search Report and Written Opinion dated Dec. 3, 2014.
PCT International Patent Application No. PCT/US2015/054756 filed Oct. 8, 2015 in the name of Quantapore, Inc., International Search Report and Written Opinion dated Jan. 6, 2016.
PCT International Patent Application No. PCT/US2015/057245 filed Oct. 23, 2015 in the name of Quantapore, Inc., International Preliminary Report on Patentability dated Nov. 15, 2016.
PCT International Patent Application No. PCT/US2015/057245 filed Oct. 23, 2015 in the name of Quantapore, Inc., International Search Report and Written Opinion dated Jan. 21, 2016.
Ramachandran, G. et al. "Current bursts in lipid bilayers initiated by colloidal quantum dots," *Applied Physics Letter*, 86:083901-1 to 083901-3, Feb. 17, 2005.
Ramsay, N. et al. "CyDNA: Synthesis and Replication of Highly Cy-Dye Substituted DNA by an Evolved Polymerase," *J. Am. Chem. Soc.*, vol. 132, 5096-5104, Mar. 2010.
Randolph, JB et al. "Stability, specificity and fluorescence brightness of multiply-labeled fluorescent DNA probes," *Nucleic Acids Research*, 25(14) 2923-2929, May 1997.
Rasnik, I. et al., "Nonblinking and long-lasting single-molecule fluorescence imaging," *Nature Methods*, 3(11), pp. 891-893, Nov. 2006.
Reed, M.A. "Quantum Dots," *Scientific American*, pp. 118-123, Jan. 1993.
Resch-Genger, U. et al. "Quantum dots versus organic dyes as fluorescent labels," *Nature Methods*, 5(9), pp. 763-775, Sep. 2008.
Rhee, M. et al., "Nanopore Sequencing Technology: Nanopore Preparations," *Trends in Biotechnology*, vol. 25, No. 4, pp. 174-181, Apr. 2007.
Rhee, M. et al., "Nanopore Sequencing Technology: research trends and applications," *Trends in Biotechnology*, vol. 24, No. 12, pp. 580-586, Dec. 2006.
Roy et al. "A practical guide to single molecule FRET," *Nature Methods*, 5(6): 507-516, Jun. 2008.
Sabanayagam, C.R. et al., "Long time scale blinking kinetics of cyanine fluorophores conjugated to DNA and its effect on Forster resonance energy transfer," *J. Chem. Phys.*, 123(22), pp. 224708-1 to 224708-7, Dec. 2005.
Sanger, F. et al., "DNA Sequencing with Chain-Terminating Inhibitors," *Proc. Natl. Acad. Sci. USA*, vol. 74, No. 12, pp. 5463-5467, Dec. 1977.
Sauer, M. et al. "Single molecule DNA sequencing in submicrometer channels: state of the art and future prospects," *Journal of Biotechnology*, 86(3), 181-201, Apr. 2001.
Schumacher, S. et al, "Highly-integrated lab-on-chip system for point-of-care multiparameter analysis," *Lab on a Chip*, 12(3), pp. 464-473, Feb. 7, 2012.
Seela, F. et al. "Fluorescent DNA: the development of 7-deazapurine nucleoside triphosphates applicable for sequencing at the single molecule level," *Journal of Biotechnology*, 86(3), 269-279, Apr. 2001.
Shaffer, C., "Next generation sequencing outpaces expectations," *Nature Biotechnology*, vol. 25, p. 149, Feb. 2007.

Shi, L. et al. "Luminescent Quantum Dots Fluorescence Resonance Energy Transfer-Based Probes for Enzymatic Activity and Enzyme Inhibitors," *Anal. Chem*, 79(1), pp. 208-214, Jan. 1, 2007.
Smolina, I.V. et al. "High-density fluorescently labeled rolling-circle amplicons for DNA diagnostics," *Analytical Biochemistry*, 347: 152-155, Jun. 21, 2005.
Song, L. et al., "Structure of Staphylococcal alpha-hemolysin, a heptameric transmembrane protein," *Science*, vol. 274, No. 5294, pp. 1859-1866, Dec. 13, 1996.
Soni, et al. "Progress toward Ultrafast DNA Sequencing Using Solid•State Nanopores," *Clinical Chemistry*, vol. 53, No. 11; pp. 1996-2001, Oct. 2007.
Soni, G. V. et al. "Synchronous optical and electrical detection of biomolecules traversing through solid-state nanopores," *Review of Scientific Instruments*, pp. 014301-1-014301-7, published online Jan. 19, 2010.
Stephan, J. et al. "Towards a general procedure for sequencing single DNA molecules," *Journal of Biotechnology*, 86(3) 255-267, Apr. 2001.
Storm, A. J. et al. "Fabrication of solid-state nanopores with single-nanometre precision," *Nature Materials*, vol. 2, pp. 537-540, Aug. 2003.
Strittmatter, W.J. et al, "Apolipoprotein E and Alzheimer's Disease," *Annual Review of Neuroscience*, vol. 19, pp. 53-77, 1996.
Stryer, L. et al. "Diffusion-enhanced fluorescence energy transfer," *Annual review of biophysics and bioengineering*, vol. 11. No. 1; pp. 203-222, 1982.
Stryer, L., "Fluorescence Energy Transfer as a Spectroscopic Ruler," *Annual Review of Biochemistry*, vol. 47, pp. 819-846, Jul. 1978.
Tamura, T., *Molecular Biology Illustrated*,revised Second Edition, pp. 174-175, Jan. 1, 2003.
Tasara, T. et al. "Incorporation of reporter molecule-labeled nucleotides by DNA polymerases. II. High-density labeling of natural DNA," *Nucleic Acids Research*, 31(10), 2636-2646, May 2003.
Telenius, H. et al., "Degenerate oligonucleotide-primed PCR: General amplification of target DNA by a single degenerate primer," *Genomics*, vol. 13, No. 3, pp. 718-725, Jul. 1992.
Thompson, J. F. et al. "The properties and applications of single-molecule DNA sequencing," *Genome Biology*, 12(217), 10 pages, Feb. 24, 2011.
Timp, W., et al, "DNA base-calling form a nanopore using a Viterbi algorithm," *Biophysical J.*, vol. 102, pp. L37-L39, May 2012.
Tucker, T. et al, "Massively Parallel Sequencing: The Next Big Thing in Genetice Medicine," *Am. J. Human Genet.*, vol. 85, pp. 142-154, Aug. 2009.
Turner, E. et al, "Methods for Genomic Partitioning," *Annual Review of Genomics and Human Genetics*, vol. 10, pp. 263-284, Sep. 2009.
U.S. Appl. No. 13/426,515, filed Mar. 21, 2012 in the name of Huber, Non-final Office Action dated Dec. 2, 2013.
U.S. Appl. No. 13/426,515, filed Mar. 21, 2012 in the name of Huber, Notice of Allowance dated Apr. 11, 2014.
U.S. Appl. No. 13/662,532, filed Oct. 28, 2012 in the name of Huber, Final Office Action dated Mar. 17, 2015.
U.S. Appl. No. 13/662,532, filed Oct. 28, 2012 in the name of Huber, Non-final Office Action dated Aug. 7, 2014.
U.S. Appl. No. 13/662,532, filed Oct. 28, 2012 in the name of Huber, Non-final Office Action dated Dec. 20, 2013.
U.S. Appl. No. 14/018,376, filed Sep. 4, 2013 in the name of Huber, Final Office Action dated Sep. 24, 2015.
U.S. Appl. No. 14/018,376, filed Sep. 4, 2013 in the name of Huber, Non-final Office Action dated Mar. 3, 2015.
U.S. Appl. No. 14/285,474, filed May 22, 2014 in the name of Huber, Non-final Office Action dated Apr. 30, 2015.
U.S. Appl. No. 14/285,474, filed May 22, 2014 in the name of Huber, Notice of Allowance dated Nov. 20, 2015.
U.S. Appl. No. 14/922,038, filed Oct. 23, 2015 in the name of Huber, Non-final Office Action dated Jan. 12, 2017.
U.S. Appl. No. 14/922,038, filed Oct. 23, 2015 in the name of Huber, Non-final Office Action dated Nov. 2, 2016.
U.S. Appl. No. 14/922,038, filed Oct. 23, 2015 in the name of Huber, Notice of Allowance dated Feb. 23, 2017.
U.S. Appl. No. 61/168,431, filed Apr. 10, 2009.

(56) References Cited

OTHER PUBLICATIONS

Venkatesan, B. M. et al. "Lipid bilayer coated Al2O3 naopore sensors: towards a hybrid biological solid-state nanopore," *Biomed Microdevices*, 13(4), 21 pages, Sep. 18, 2011.
Venkatesan, B. M. et al. "Nanopore sensors for nucleic acid analysis," *Nature Nanotechnology*, vol. 6, pp. 615-624, Oct. 2011.
Vercoutere, W. et al., "Rapid discrimination among individual DNA hairpin molecules at single-nucleotide resolution using an ion channel," *Nature Biotechnology*, vol. 19, pp. 248-252, Mar. 2001.
Voelkerding, K. et al, "Next-Generation Sequencing: From Basic Research to Diagnostic," *Clinical Chemistry*, 55:4, pp. 641-658, Apr. 2009.
Walker, B. et al. "Key Residues for Membrane Binding, Oligomerization, and Pore Forming Activity of Staphylococcal alpha-Hemolysin Identified by Cysteine Scanning Mutagenesis and Targeted Chemical Modification," *Journal of Biological Chemistry*, 270(39), pp. 23065-23071, Sep. 29, 1995.
Wang, H. et al., "Nanopores with a spark for single-molecule detection," *Nature Biotechnology*, vol. 19, pp. 622-633, Jul. 2001.
Wanunu, M. et al. "Chemically Modified Solid-State Nanopores," *Nano Letters*, 7(6), pp. 1580-1585, May 16, 2007.
Wanunu, M. et al."Nanopores: A journey towards DNA sequencing," *Physics of Life Reviews*, vol. 9, pp. 125-158, Jun. 2012.
White et al., "Single Ion-Channel Recordings Using Glass Nanopore Membranes," *J. Amer. Chem. Soc.*, 129:11766-11775, Sep. 5, 2007.
Won, J. et al. "Protein polymer drag-tags for DNA separations by end-labeled free solution electrophoresis," *Electrophoresis*, vol. 26, pp. 2138-2148, Jun. 2005.
Wu, X. et al, "Microfluidic differential resistive pulse sensors," *Electrophoresis*, 29(13), pp. 2754-2759, Jun. 2008.
Xu, et al., "Perspectives and Challenges of Emerging Single-Molecule DNA Sequencing Technologies," *SMALL*, 5(53), pp. 2638-2649, Dec. 4, 2009.
Yan, X. et al, "Parallel Fabrication of Sub-50-nm Uniformly Sized Nanaparticles by Deposition through a Patterned Silicon Nitride Nanostencil," *Nano Letters*, 5(6), pp. 1129-1134, Jul. 2005.
Yang, J. et al. "Rapid and precise scanning helium ion microscope milling of solid-state nanopores for biomolecule detection," *Nanotechnology*, vol. 22, 6 pages, Jun. 10, 2011.
Yu, H. et al. "Cyanine dye dUTP analogs for enzymatic labeling of DNA probes," *Nucleic Acids Research*, 22(15), 3226-3232, Apr. 1994.
Yu, Y. et al. "Facile preparation of non-self-quenching fluorescent DNA strands with the degree of labeling up to the theoretic limit," *Chem. Commun.*, vol. 48, 6360-6362, May 2012.
Zhang, L. et al., "Whole genome amplification from a single cell: implications for genetic analysis," *Proc. Natl. Acad. Sci. USA*, vol. 89, No. 13, pp. 5847-5851, Jul. 1, 1992.
Zhe, J. et al, "A micromachined high throughput Coulter counter for bioparticle detection and counting," *J. Micromech. Microeng.*, vol. 17, pp. 304-313, Jan. 11, 2007.
Zheng, S. et al. "Parallel analysis of biomolecules on a microfabricated capillary array chip," *Electrophoresis*, vol. 26, abstract only, Mar. 2006.
Zhu, Z. et al."Directly labeled DNA probes using fluorescent nucleotides with different length linkers," *Nucleic Acids Research*, 22(16), 3418-3422, Aug. 1994.
Zwolak, M. et al., "Colloquium: Physical approaches to DNA sequencing and detection," *Reviews of Modern Physics*, 80(1), pp. 141-165, Jan. 2, 2008.

1 nanopore within resolution limited area

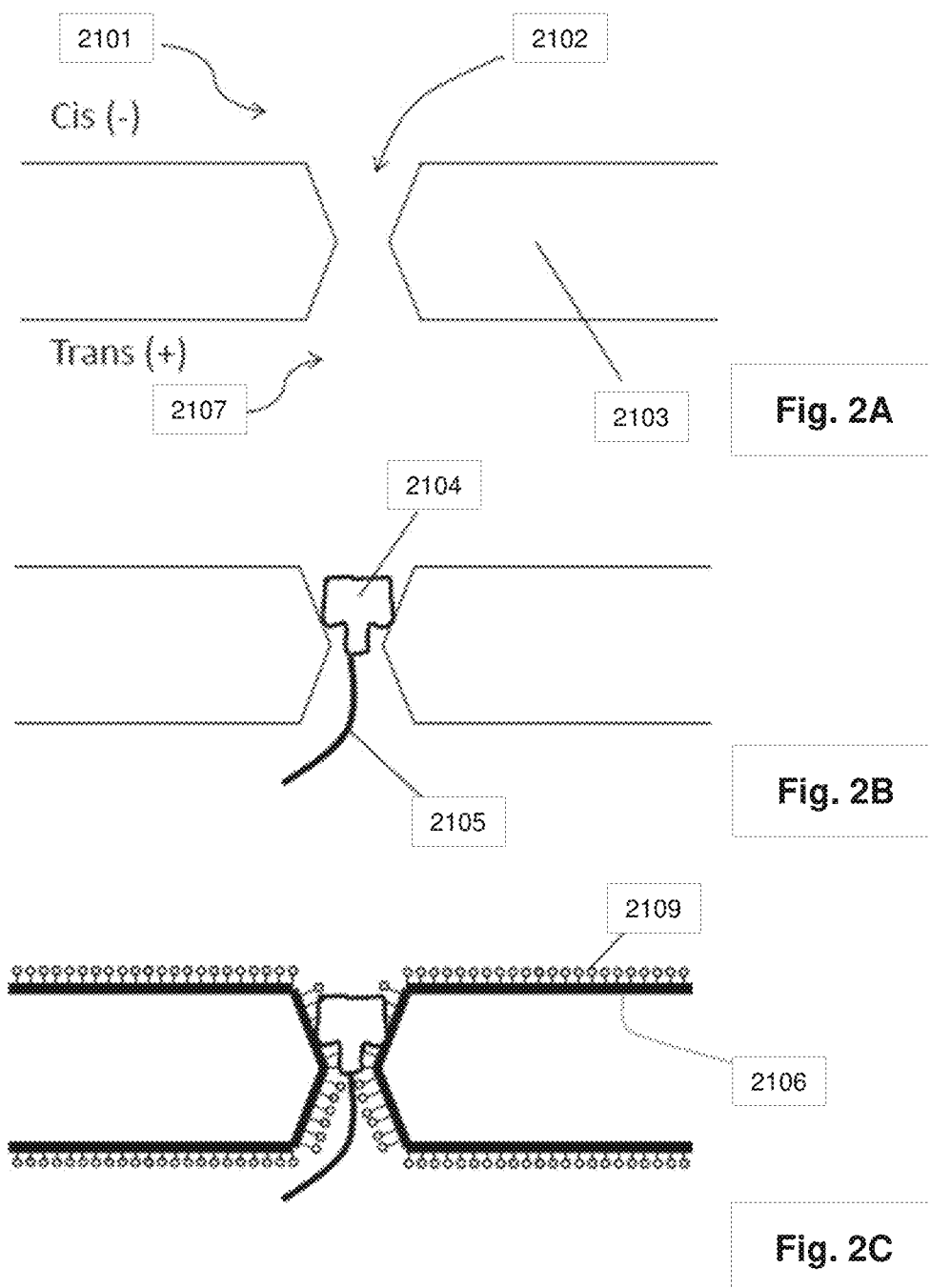

EFFICIENT OPTICAL ANALYSIS OF POLYMERS USING ARRAYS OF NANOSTRUCTURES

CROSS REFERENCE TO RELATED APPLICATIONS

This application is a continuation of U.S. patent application Ser. No. 15/453,542, filed Mar. 8, 2017, which is a continuation of U.S. patent application Ser. No. 14/922,038, filed Oct. 23, 2015, now U.S. Pat. No. 9,624,537, which claims priority from U.S. Provisional Application Ser. No. 62/068,599 filed Oct. 24, 2014, all of which are hereby incorporated by reference in their entireties.

BACKGROUND

DNA sequencing technologies developed over the last decade have revolutionized the biological sciences, e.g. Lerner et al, The Auk, 127: 4-15 (2010); Metzker, Nature Review Genetics, 11: 31-46 (2010); Holt et al, Genome Research, 18: 839-846 (2008); and have the potential to revolutionize many aspects of medical practice in coming years, e.g. Voelkerding et al, Clinical Chemistry, 55: 641-658 (2009); Anderson et al, Genes, 1: 38-69 (2010); Freeman et al, Genome Research, 19: 1817-1824 (2009); Tucker et al, Am. J. Human Genet., 85: 142-154 (2009). However, to realize such potential there are still a host of challenges that must be addressed, including reduction of per-run sequencing cost, simplification of sample preparation, reduction of run time, increasing sequence read lengths, improving data analysis, and the like, e.g. Baker, Nature Methods, 7: 495-498 (2010); Kircher et al, Bioessays, 32: 524-536 (2010); Turner et al, Annual Review of Genomics and Human Genetics, 10: 263-284 (2009). Single molecule sequencing on nano-fabricated arrays, such as nanopore arrays, may address some of these challenges, e.g., Maitra et al, Electrophoresis, 33: 3418-3428 (2012); Venkatesan et al, Nature Nanotechnology, 6: 615-624 (2011); however, these approaches have their own set of technical difficulties, such as, reliable nanostructure fabrication, control of DNA translocation rates through nanopores, nucleotide discrimination, detection of electrical signals from large arrays of nanopore sensors, and the like, e.g. Branton et al, Nature Biotechnology, 26(10): 1146-1153 (2008); Venkatesan et al (cited above).

Optical detection of nucleotides has been proposed as a potential solution to some of the technical difficulties in the field of nanopore sequencing, e.g. Huber, International patent publication WO 2011/040996; Russell, U.S. Pat. No. 6,528,258; Pittaro, U.S. patent publication 2005/0095599; Joyce, U.S. patent publication 2006/0019259; Chan, U.S. Pat. No. 6,355,420; McNally et al, Nano Lett., 10(6): 2237-2244 (2010); and the like, and has been implemented in the field of single-molecule sequencing using arrays of zero mode waveguides, e.g. Eid et al, Science, 323: 133-138 (2009). However, a limitation of optically-based nanopore and zero mode waveguide sequencing relates to the resolution limits of optical detection systems. Although current nanoscale fabrication techniques are capable of producing arrays of sub-10 nm pores and wells with comparable pore-to-pore or well-to-well spacing, the full potential of such arrays cannot be used to advantageously achieve higher throughput rates because of the resolution limit of the optical detection systems.

In view of the above, it would be advantageous to nanopore sensor technology in general and its particular applications, such as optically based nanopore sequencing and/or zero mode waveguide sequencing, if methods were available for ameliorating the limitations imposed by detection resolution limits.

SUMMARY OF THE INVENTION

The present invention is directed to devices and methods for efficient optical detection and analysis of polymers, such as polynucleotides, using high density arrays of nanostructures, such as nanopores or nanowells.

In some embodiments, the invention is directed to methods and apparatus for detecting sequences of optical signals from parallel reactions on an array, wherein apparatus of the invention comprise the following elements: (a) an array of nanostructures each comprising a reaction site and each capable of confining a reaction that generates a sequence of optical signals, the nanostructures of the array being arranged in clusters each comprising a number of nanostructures and each different cluster of nanostructures being disposed within a different resolution limited area; and (b) an optical system operatively associated with the array for detecting optical signals from the reactions. In some embodiments, the number of nanostructures in each cluster is either greater than one or a random variable with an average value greater than zero. In some of the foregoing embodiments, polymers being analyzed comprise polynucleotides and such polynucleotides are translocated through the nanopores electrophoretically from a "cis" chamber to a "trans" chamber.

In other embodiments, the invention includes a method of sequencing polynucleotides each having a plurality of optical labels attached to a sequence of nucleotides, the method comprising the following steps: (a) translocating single stranded polynucleotides at a concentration and flux through a nanopore array, wherein substantially every nucleotide of each single stranded polynucleotides has an optical label attached, the optical label capable of generating an optical signal indicative of the nucleotide to which it is attached, and wherein the nanopore array comprises clusters of nanopores, such that nanopores of different clusters are within different resolution limited areas; (b) exposing the optical labels of each nucleotide to excitation radiation upon exiting a nanopore; (c) measuring in each resolution limited region on the nanopore array optical signals generated by optical labels exiting nanopores to identify the nucleotide to which the optical label is attached whenever such optical signals are from a single optical label; and (d) determining a nucleotide sequence of the polynucleotide from a sequence of optical signals from single optical labels. In some embodiments of the above, the pluralities of nanopores within the resolution limited areas, concentration of the polynucleotides, and/or flux of the polynucleotides through said nanopore array are selected to maximize the number of sequence-able nanopores in the array. In other embodiments of the above method, the flux and/or movement of the single stranded polynucleotides through the nanopore array is controlled to maximize the number of sequence-able nanopores in the array by controlling an electrical potential across the nanopore array. That is, in some embodiments, during a sequencing operation an electrical potential across the nanopore array is varied in order to maximize sequencing throughput, e.g. by maximizing the total number of sequence-able nanopores in the array.

The present invention is exemplified in a number of implementations and applications, some of which are summarized below and throughout the specification.

BRIEF DESCRIPTION OF THE DRAWINGS

FIGS. 2A-2C illustrate an embodiment of a hybrid nanopore.

DETAILED DESCRIPTION OF THE INVENTION

Figure 1A:
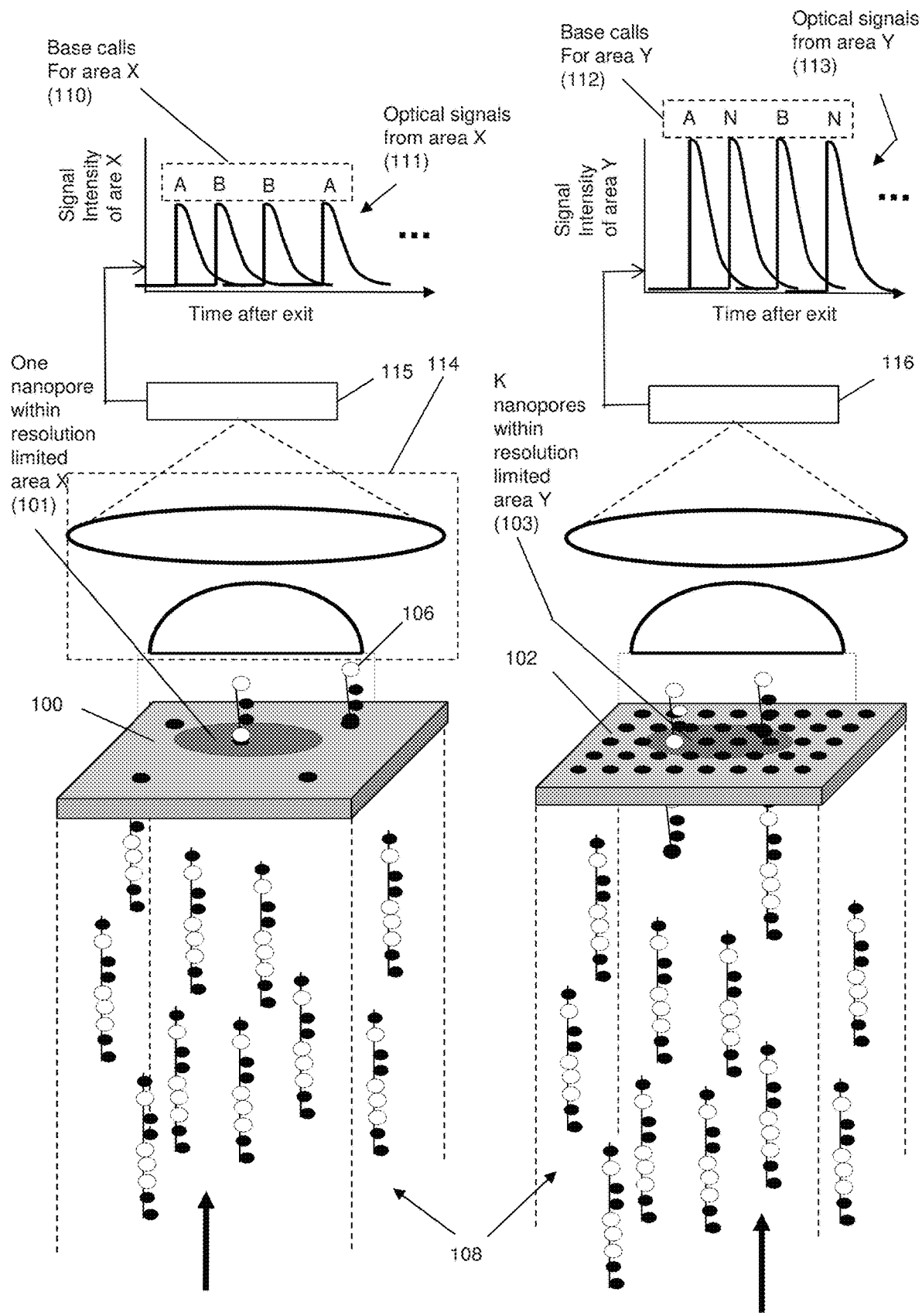
FIG. 1A illustrate the limitations of optical detection of nanopore events in face of signal resolution limits.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention. For example, particular nanopore types and numbers, particular labels, FRET pairs, detection schemes, fabrication approaches of the invention are shown for purposes of illustration. It should be appreciated, however, that the disclosure is not intended to be limiting in this respect, as other types of nanopores, arrays of nanopores, and other fabrication technologies may be utilized to implement various aspects of the systems discussed herein. Guidance for aspects of the invention is found in many available references and treatises well known to those with ordinary skill in the art, including, for example, Cao, Nanostructures & Nanomaterials (Imperial College Press, 2004); Levinson, Principles of Lithography, Second Edition (SPIE Press, 2005); Doering and Nishi, Editors, Handbook of Semiconductor Manufacturing Technology, Second Edition (CRC Press, 2007); Sawyer et al, Electrochemistry for Chemists, $2^{nd}$ edition (Wiley Interscience, 1995); Bard and Faulkner, Electrochemical Methods: Fundamentals and Applications, $2^{nd}$ edition (Wiley, 2000); Lakowicz, Principles of Fluorescence Spectroscopy, $3^{rd}$ edition (Springer, 2006); Hermanson, Bioconjugate Techniques, Second Edition (Academic Press, 2008); and the like, which relevant parts are hereby incorporated by reference.

The invention is directed to methods and devices for efficient polymer analysis using dense arrays of nanoscale structures, such as nanopores, nanowells, nanoparticles, or the like, coupled with optical detection systems. In some embodiments, polymers of interest are linear polymers comprising sequences of at least two different kinds of monomer linked in a linear chain with substantially every one of at least one kind of monomer being labeled with an optical label capable of generating an optical signal indicative of the monomer to which it is attached. In other embodiments, polymers of interest are linear polymers comprising sequences of at least two different kinds of monomer linked in a linear chain with substantially every monomer of each kind being labeled with an optical label capable of generating an optical signal indicative of the monomer to which it is attached. In still other embodiments, polymers of interest are polynucleotides which capable of participating in a reaction that generates a sequence of optical signals that contains information about the nucleotide sequence of such polynucleotide. Polymers of particular interest are polynucleotides, especially single stranded DNAs. Also of particular interest are DNA polymers whose nucleotides are labeled with fluorescent dyes, such as fluorescent dyes from a mutually quenching set. In one aspect, the invention provides methods and devices to determine monomer sequences of complete or partial polymers in a sample. In another aspect, the invention provides methods to determine an optical signature, or fingerprint, of a polymer or polynucleotide in a sample. Methods and devices of the invention address the problem of efficient use of high capacity nanopore or nanowell arrays in view of the resolution limits of optical detection. Methods and devices of the invention also address the problem of loss of data acquisition capability caused by nonfunctional nanopores or nanowells, which may be caused by a variety of conditions, including but not limited to, membrane failures or defects from fabrication errors, inactive enzymes, such as, inactive or mis-attached polymerases, and when protein nanopores are employed, protein mis-folding, subunit mis-aggregation, inoperable orientation of the protein nanopore in a membrane, and the like.

As used herein, a "resolution limited area" is an area of a surface of a nanopore or nanowell array within which individual features or light emission sources cannot be distinguished by an optical signal detection system. Without intending to be limited by theory, such resolution limited area is determined by a resolution limit (also sometimes referred to as a "diffraction limit" or "diffraction barrier") of an optical system. Such limit is determined by the wavelength of the emission source and the optical components and may be defined by d=λ/NA, where d is the smallest feature that can be resolved, λ is the wavelength of the light and NA is the numerical aperture of the objective lens used to focus the light. Thus, whenever two or more nanopores are within a resolution limited area and two or more optical signals are generated at the respective nanopores, an optical detection system cannot distinguish or determine which optical signals came from which nanopore. In accordance with the invention, a surface of a nanopore array may be partitioned, or subdivided, into non-overlapping regions, or substantially non-overlapping regions, corresponding to resolution limited areas. The size of such subdivisions corresponding to resolution limited areas may depend on a particular optical detection system employed. In some embodiments, whenever light emission sources are within the visible spectrum, a resolution limited area is in the range of from 300 nm$^2$ to 3.0 μm$^2$; in other embodiments, a resolution limited area is in the range of from 1200 nm$^2$ to 0.7 μm$^2$; in other embodiments, a resolution limited area is in the range of from 3×10$^4$ nm$^2$ to 0.7 μm$^2$, wherein the foregoing ranges of areas are in reference to a surface of a nanopore or nanowell array. In some embodiments, the visible spectrum means wavelengths in the range of from about 380 nm to about 700 nm.

An average number of active nanopores in a nanopore array may be estimated as follows. Let $\alpha$ be the fraction of nanopores that are functional; let t be the average transit time of a polymer through a nanopore; and let w be the average wait time to the next polymer, or polymer fragment. If a nanopore is defined as "active" whenever it is currently translocating a polymer, then an expression for the active fraction of nanopores, u, may be given as follows:

$$u=\alpha t/(w+t)$$

This expression suggests that u could be increased by increasing $\alpha$ or t or by reducing, w. For example, $\alpha$ could be increased by improving manufacture of the nanopore arrays, t could be increased by increasing the length of polymer analyzed, and w could be reduced by increasing the flux of polymer across the nanopore array, for example, by increasing concentration of polymer and/or increasing the polymer driving force, e.g. an electric potential across the array, in the case of DNA. As noted above, these approaches to increasing the efficiency of a nanopore array are limited because, although they may lead to a greater number or density of active nanopores, whenever two or more nanopores are active within a resolution limited area the resulting signals do not provide useful information. Therefore, in one aspect, the method of the invention provides values of u that maximize the number of nanopores providing useful information in view of constraints imposed by the limits on resolution. In one aspect, nanopores capable of providing useful sequence information are those which are the only active nanopore within a resolution limited area, referred to herein as "sequence-able nanopore." That is, a sequence-able nanopore is one which does not have other active nanopores within the same resolution limited area at the same time. For nanopores spaced in a square array, the number sequence-able nanopores may be estimated as follows.

Assume an embodiment with a square of clusters of nanopores of area, A, with distance, d, between clusters, where d is the diffraction limit that defines a resolution limited area. The number of clusters is then $A/d^2=4270$ clusters. The fraction, p1, of clusters that have exactly one active nanopore (i.e. exactly one sequence-able nanopore) is given by $p1=ku(1-u)^{k-1}$, where again u is the active fraction of nanopores. The total number of sequence-able pores is on average, $Ap1/d^2$, or $kAu(1-u)^{k-1}/d^2$. For example, if u is fixed at u=0.2, the foregoing expression for p1 is maximized with k=4 and k=5. For illustration, if u is fixed at u=0.2 and the number of clusters is 1000, the value of p1 is maximized when k=4 or k=5. Taking k=4, the total number of pore will be 4000, and the number of sequence-able pores will be 410 on average. For comparison, a grid of single pores with the same spacing d will have just 1000 pores, and the number of sequence-able pores will be only 200 on average. Thus in the example the invention achieves more than double the throughput of an ordinary grid.

FIG. 1A, which is not intended to represent the actual physical or chemical condition adjacent to a nanopore array, shows two solid phase membranes: membrane (100) having a single nanopore within resolution limited area (101) and membrane (102) having a plurality, K, of nanopores within resolution limited area (103). Below, membranes (100) and (102) are shown polymers (108) consisting of two differently labeled monomers (represented as linked black and white circles). Polymers (108) have an average length, concentration and flux across membranes (100) and (102). A flux of polymers (108) may be produced by a variety of methods, for example, when polymers are polynucleotides, a flux may be produced by an electric field. Optical labels on monomers of polymers (108) are excited to generate optical signals as each monomer exits from a nanopore of membranes (100) and (102). For example, when optical labels are fluorescent labels, such as FRET acceptors, such excitation may be accomplished using a total internal reflectance fluorescence (TIRF) microscope system as a detection system, as illustrated diagrammatically by (114). Fluorescent labels may be excited directly or indirectly using FRET donor-acceptor pairs. For each resolution limited area, detectors (115) and (116) collect optical signals and convert them into values that can be displayed, such as the curves representing optical signals from resolution limited area X (111) and the curves representing optical signals from resolution limited area Y (113). In some embodiments, an objective of the analytical systems illustrated in FIG. 1A is to use the optical signals generated by the optical labels to identify sequences of monomers among polymers (108). This may be accomplished readily in the case where a single operable nanopore is within a resolution limited area, as shown by (101). However, when more than one nanopore is within a resolution limited area and more than one polymer translocates through such nanopores causing multiple optical signals to be generated, the recorded signals, such as (113), lose information from which monomer sequences can be determined. Thus, for example, in the single nanopore case, base (or monomer) calls can be made successfully in a 2-label system; that is, A, B (i.e. "not-A"), B and A (110); whereas, in the multiple nanopore case, base calls cannot be made successfully; that is, the calls would be A, N, B and N, where the two "N" calls correspond to mixed optical signals whose components cannot be assigned to a particular nanopore within resolution limited area (103).

Figure 1B:
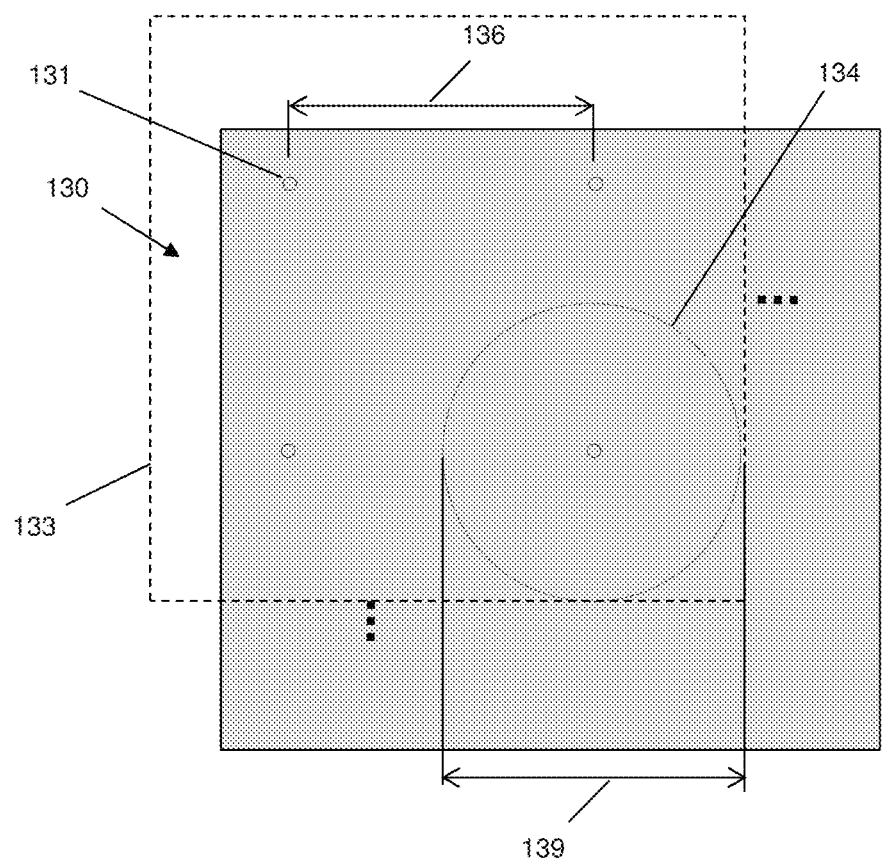
FIGS. 1B-1E illustrate various nanopore array configurations related to signal resolution limits.
Figure 1C:
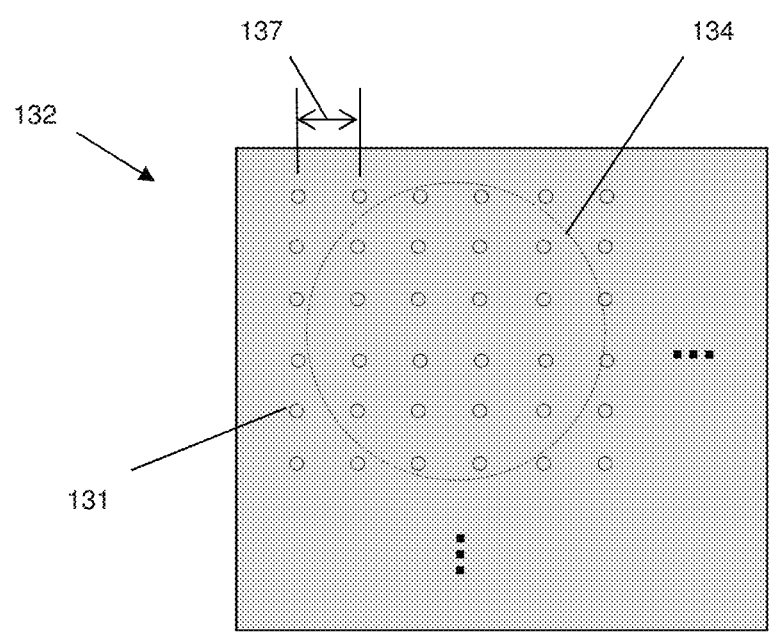

As mentioned above, the problem of multiple nanopores within a resolution limited area may be addressed by fabricating nanopore arrays so that the density of nanopores is sufficiently low that there is a maximum of a single nanopore within each resolution limited area, as illustrated in FIG. 1B. There nanopores (131) of a portion of nanopore array (130) are spaced (136) so that there is only one nanopore within a resolution limited area (134) having diameter (139). Unfortunately, such an approach is not efficient and does not take advantage of fabrication capabilities that permit much higher densities of nanopores, as illustrated in FIG. 1C, where nanopores (131) of a portion of nanopore array (132) are spaced (137) so that there multiple nanopores within a resolution limited area (134). The lack of efficiency is particularly exacerbated when hybrid nanopores are employed that comprise a solid phase membrane with fabricated apertures containing protein nanopores immobilized therein, e.g. as described in Huber et al, U.S. patent publication US2013/0203050, which is incorporated herein by reference. Although hybrid nanopores are very useful because of the highly regular bores or lumens of the immobilized proteins, only a fraction of the immobilized protein nanopores may be functional, or operable; that is, only a fraction have unobstructed bores that provide a fluid communication path between two chambers separated by a solid phase membrane (referred to herein as an "operable fraction" or "functional fraction"). Typically protein nanopores of an array of hybrid nanopores have an operable fraction in the range of from 10-50 percent, and frequently have an operable fraction of about 25 percent. For such nanopore arrays, the inefficiency of the arrangement shown in FIG. 1B is readily apparent: a large fraction of the array would be inoperable and therefore useless.

Figure 1D:
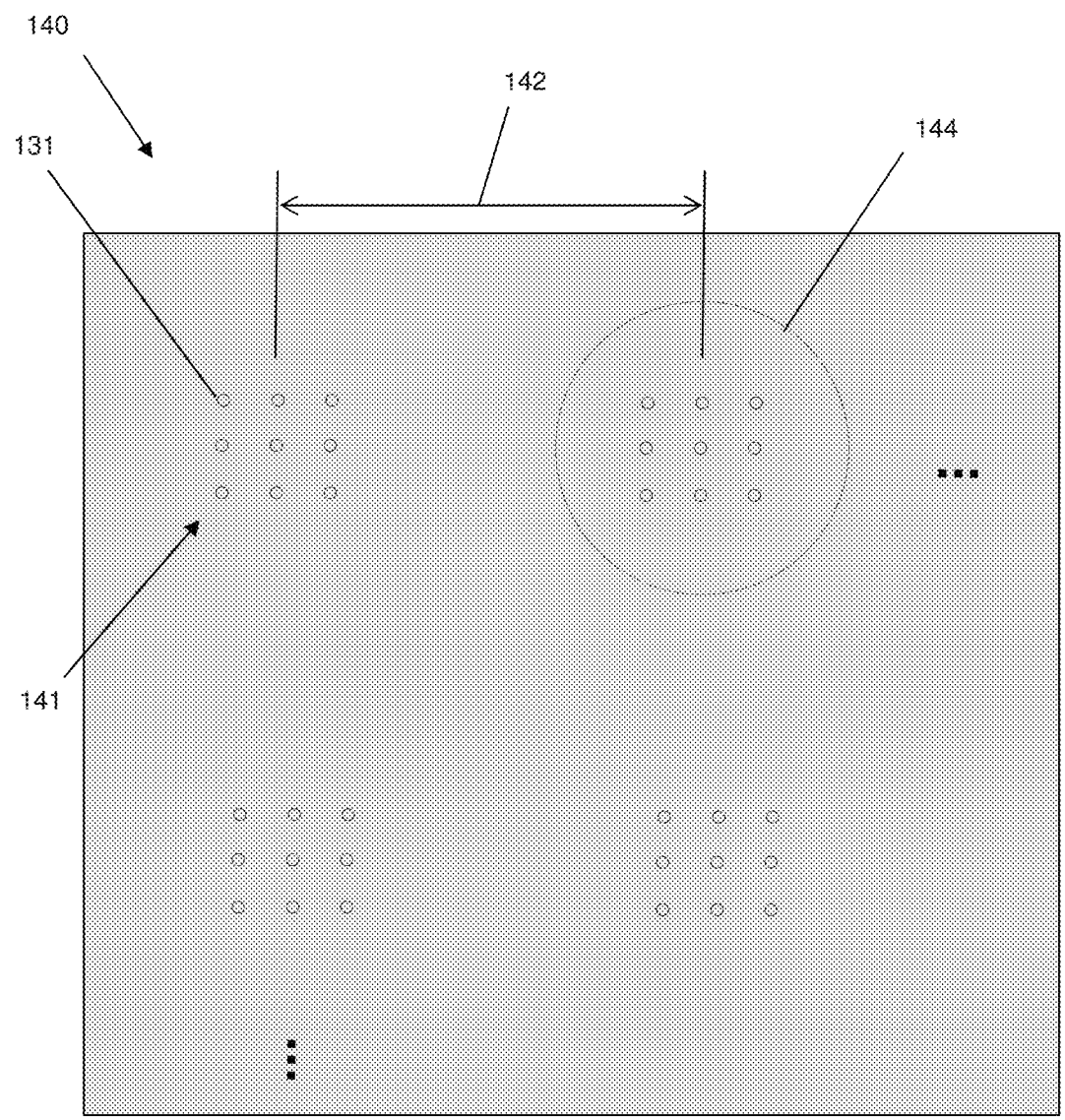
Figure 1E:
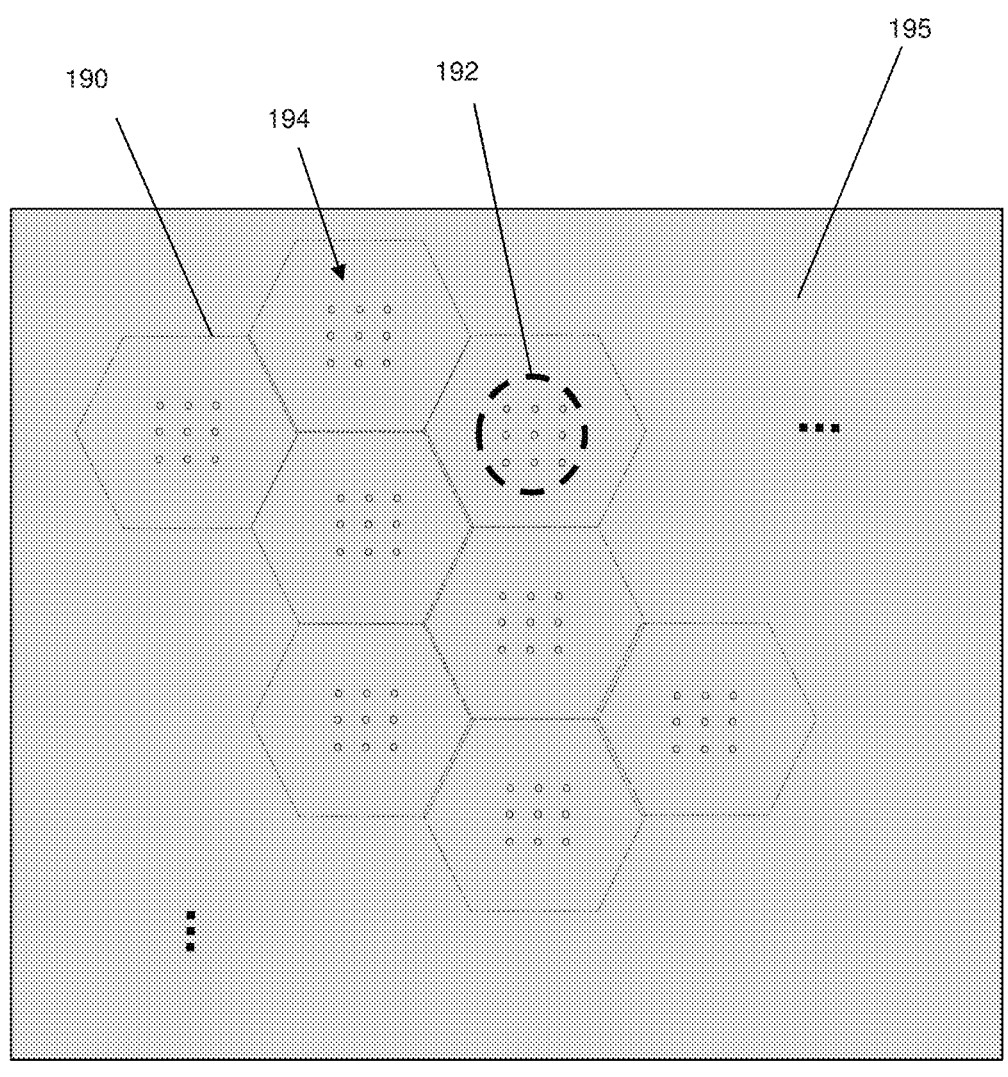

This problem may be addressed by providing arrays of clusters of nanopores, as illustrated by FIGS. 1D (showing a rectilinear array of clusters) and 1E (showing a hexagonal array of clusters). In part, the present invention is based on the recognition and appreciation that sequencing throughput per unit area of nanopore array may be increased by employing nanopore arrays that are arrays of clusters of nanopores wherein each cluster contains a plurality of nanopores and wherein the cluster-to-cluster distance is approximately equal to the diffraction limit distance. Stated another way, nanopores in different clusters are in different resolution limited areas. One of ordinary skill would recognize that this principle may be applied to any array of nanostructures, such as nanowells or nanoparticles, that are used to generate sequences of optical signals. Returning to FIGS. 1D and 1E, portion of nanopore array (140) shows clusters (141) of a plurality of nanopores (or apertures) (131), where clusters (141) are spaced with an inter-cluster distance (142) sufficiently great that each cluster may be within a separate resolution limited area (144) and nanopores of different clusters do not share a resolution limited area. In one embodiment, a plurality of nanopores is selected so that the average number of operable nanopores is between 1 and 2. In another embodiment, the plurality of nanopores within a cluster is in the range of from 2 to 9; in still another embodiment, the plurality of hybrid nanopores within a cluster is in the range of from 2 to 6. Likewise, clusters of nanopores may be arranged into a hexagonal array (140) as shown in FIG. 1E. In such an array, surface (195), for example, of a solid phase membrane, is partitioned into hexagonal regions (for example, 190) having areas substantially equal to resolution limited areas (192) and each containing a cluster of nanopores (194). In some embodiments, in arrays of clusters of nanostructures, inter-nanostructure distances within a cluster may be in the range of from 10-200 nm and inter-cluster distances (for example, a center-to-center distance) may be at least 500 nm, or at least 1 μm. In other embodiments, inter-cluster distances may be in the range of from 500 nm to 10 μm, or from 1 μm to 10 μm.

Figure 4A:
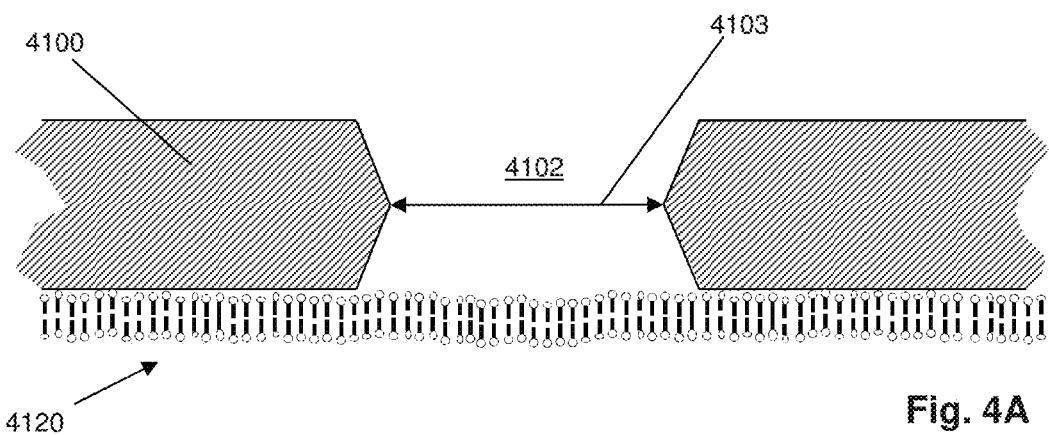
FIGS. 4A-4F illustrate dusters of labeled protein nanopores disposed in lipid bilayers across apertures in a solid phase membrane.
Figure 4B:
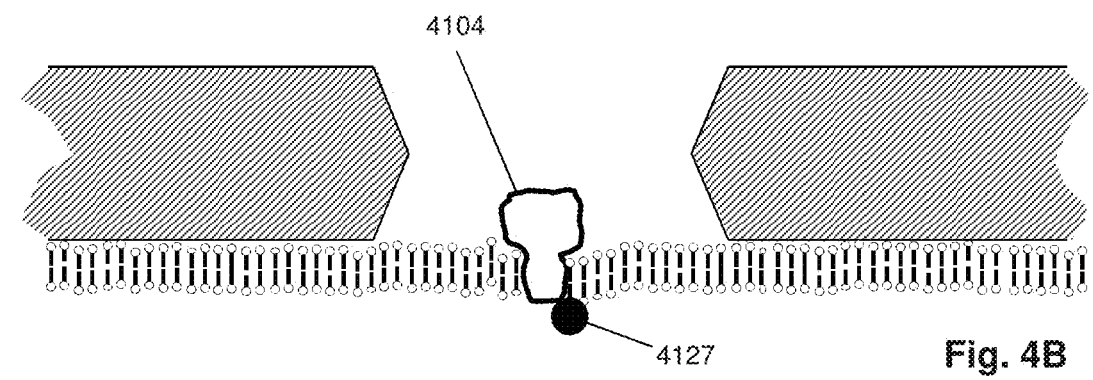
Figure 4C:
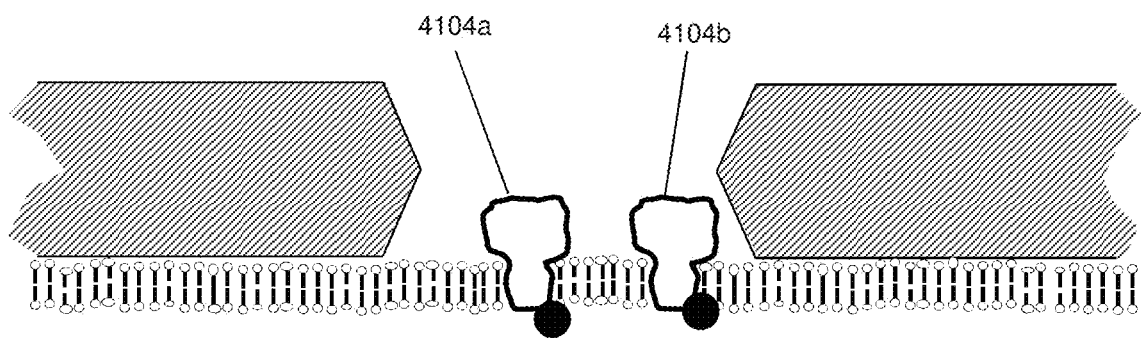
Figure 4D:
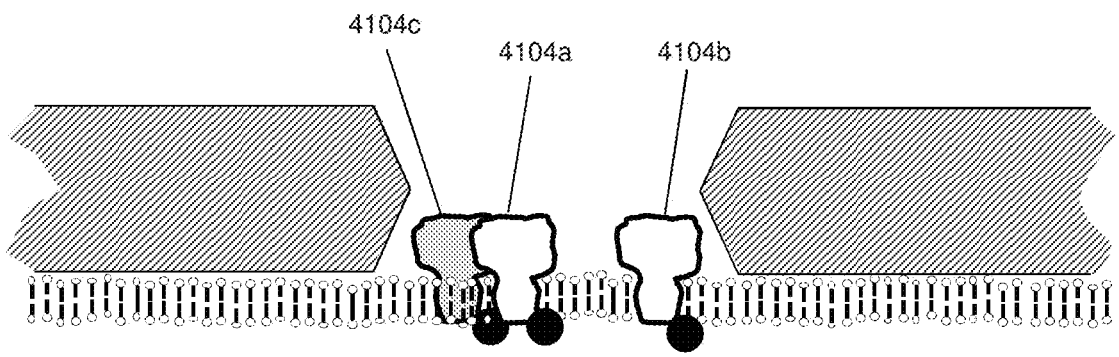
Figure 4E:
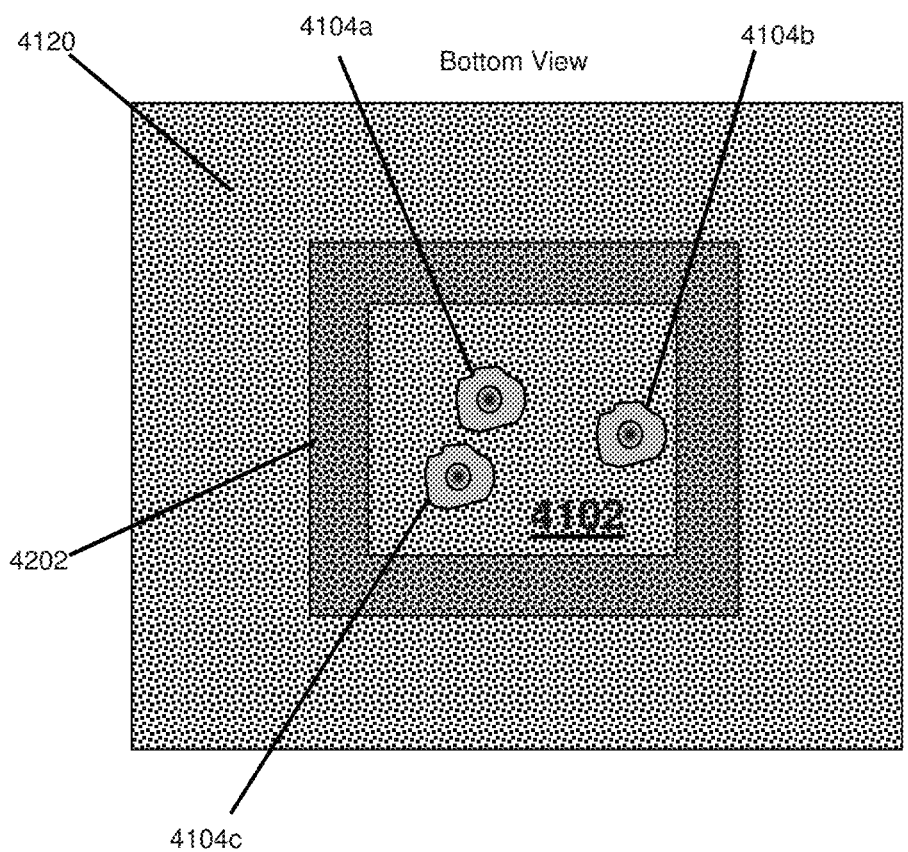
Figure 4F:
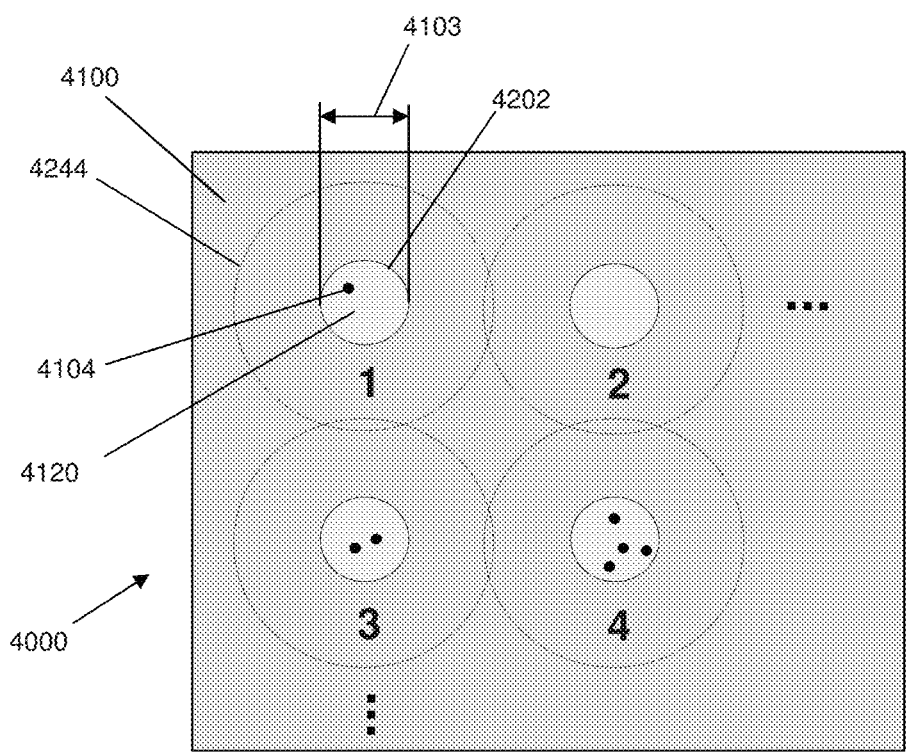

In some embodiments, clusters may also be formed by disposing protein nanopores in lipid bilayers supported by solid phase membrane containing an array (4000) of apertures, for example, as illustrated in FIG. 4F. For example, array (4000) may comprise apertures fabricated (e.g. drilled, etched, or the like) in solid phase support (4100 in FIG. 4F and 4102 in FIG. 4A). The geometry of such apertures may vary depending on the fabrication techniques employed. For example, such apertures (4202) in FIG. 4F are depicted as circular and aperture (4202) in FIG. 4E is depicted as rectangular. In some embodiments, each such aperture is associated with, or encompassed by, a separate resolution limited area (4244), as illustrated in FIG. 4F; however, in other embodiments, multiple apertures may be within the same resolution limited area. The cross-sectional area of the apertures may vary widely and may or may not be the same as between different clusters, although such areas are usually substantially the same as a result of conventional fabrication approaches. In some embodiments, apertures have a minimal linear dimension (4103) (e.g. diameter in the case of circular apertures) in the range of from 10 to 200 nm, or have areas in the range of from about 100 to $3 \times 10^4$ nm$^2$. Across the apertures is disposed a lipid bilayer, illustrated in cross-section in FIGS. 4A-4D. In some embodiments, such lipid bilayer (4120) is disposed over one surface of solid phase membrane (4100). In some embodiments, protein nanopores (4104 in FIGS. 4A-4F) are inserted into portions of lipid bilayer (4120) spanning the apertures, where in some embodiments, such as those depicted, protein nanopores may be directly labeled (4127), e.g. with a FRET donor. In some embodiments, such protein nanopores are inserted from solution in a chamber on one side of solid phase membrane (4100), which results in a random placement of protein nanopores into the aperture, such that different apertures may receive different numbers of protein nanopores, as illustrated in FIGS. 4A-4D, where apertures are shown with no, one, two, or three protein nanopores. The distribution of protein nanopores per aperture may be varied, for example, by controlling the concentration of protein nanopores during inserting step. As illustrated in FIG. 4F, in such embodiments, clusters of nanopores may comprise a random number of nanopores, for example, as shown by the representative clusters (1 through 4) where cluster 1 contains a single protein nanopore (4104), cluster 2 contains no protein nanopore, cluster 3 contains two protein nanopores, and cluster 4 contains four protein nanopores. In some embodiments, in which protein nanopores insert randomly into apertures, clusters containing one or more apertures on average have a number of protein nanopores that is greater than zero; in other embodiments, such clusters have a number of protein nanopores that is greater than 0.25; in other embodiments, such clusters have a number of protein nanopores that is greater than 0.5; in other embodiments, such clusters have a number of protein nanopores that is greater than 0.75; in other embodiments, such clusters have a number of protein nanopores that is greater than 1.0.

The effect of using arrays of clusters may be illustrated by considering the expected number of operable nanopores per unit area, such as area (133) in FIG. 1B containing four nanopores, each in a separate resolution limited area. In this configuration, if the fraction of operable nanopores is 0.25, then the expected number of operable nanopores in area (133) is simply E=4×(0.25)=1. With clusters of 2 nanopores the expected number of operable nanopores per cluster follows a binomial distribution as follows: E=0×P[n=0]+1×P[n=1]+2×P[n=2], where P[n=i] is the probability that a cluster has i operable nanopores. Thus, for clusters of 2 nanopores, the expected number of operable nanopores is 0.5, when the operability rate is 0.25.

Figure 1F:
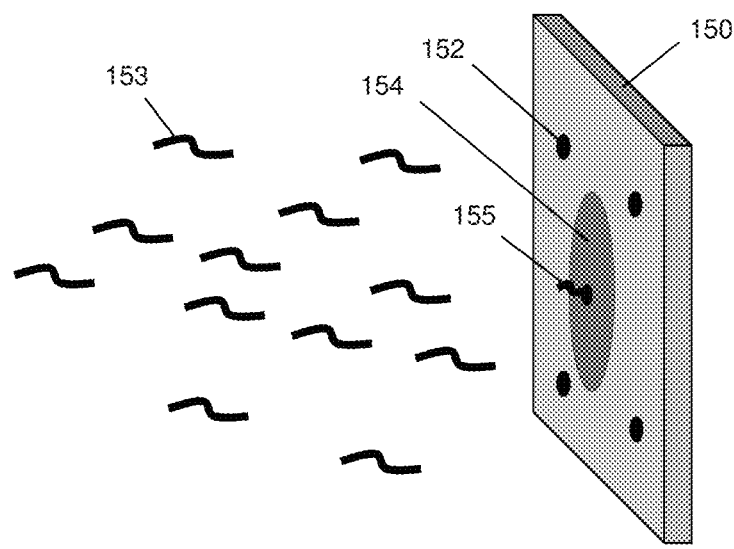
FIGS. 1F-1G illustrate analyte arrival times and signal acquisition rates for resolution limit areas or regions.
Figure 1G:
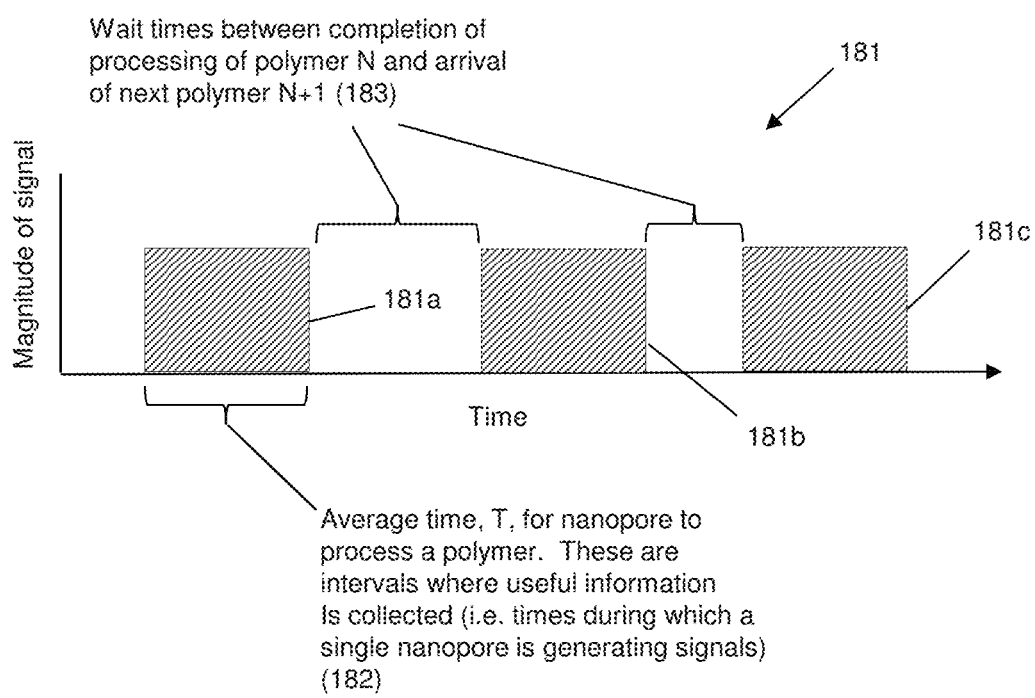

FIG. 1F shows solid phase membrane (150) with an array of nanopores (152) spaced so that there is only a single nanopore within resolution limited area (154) (a configuration similar to that of (100) of FIG. 1A). At any given nanopore entrance, polymers (153) will be captured (155) at random times. For example, the arrival of such polymers (155) may be modeled as Poisson counting process wherein the sequence of interarrival times is exponentially distributed, which roughly means the higher the concentration and flux of polymers the shorter the interarrival time. In FIG. 1G (illustrating signals (181a, 181b, 181c) generated by a sequence of captured polymers processed by a nanopore), if it is assumed that each polymer has the same length, then polymer processing time (or equivalently nanopore occupancy time) may be represented as constant length segments (182). Times between polymers (183) are the wait times during which a nanopore is inactive and not generating optical signals. After a polymer completes its translocation of a nanopore, the nanopore ceases to generate optical signals for a time until the next polymer arrives. The duty cycle of a single nanopore per resolution limited area may approach 100 percent by raising the concentration and/or flux, thereby forcing wait times to approach zero, but the information rate, because there is only one nanopore per resolution limited area, obtained per unit area of nanopore array is limited. In the same area a higher rate of information acquisition is possible by using multiple nanopores per resolution limited area by adjusting polymer concentration, magnitude of polymer flux to the solid phase membrane, and average polymer length.

In some embodiments, the invention is directed to methods of determining a nucleotide sequence of at least one polynucleotide which comprises the following steps: (a) translocating single stranded polynucleotides at a concentration and flux through a nanopore array, wherein substantially every nucleotide of each single stranded polynucleotides is labeled with an optical label capable of generating an optical signal indicative of the nucleotide to which it is attached, and wherein the nanopore array comprises clusters of nanopores, each cluster comprising a plurality of nanopores within a resolution limited area such that nanopores of different clusters are within different resolution limited areas; (b) exposing the optical labels of each nucleotide to excitation radiation upon exiting a nanopore; (c) measuring in each resolution limited region on the nanopore array optical signals generated by optical labels exiting nanopores to identify the nucleotide to which the optical label is attached whenever such optical signals are from a single optical label; and (d) determining a nucleotide sequence of the polynucleotide from a sequence of optical signals from single optical labels. In further embodiments, the density or magnitude of the pluralities of nanopores within resolution limited areas, target polynucleotide concentration, and/or flux of target polynucleotide through the nanopore array are selected to maximize the number of sequence-able nanopores in the array.

Nanopores and Nanopore Sequencing

Nanopores used with the invention may be solid-state nanopores, protein nanopores, or hybrid nanopores comprising protein nanopores or organic nanotubes such as carbon nanotubes, configured in a solid-state membrane, or like framework. Important features of nanopores include (i) constraining analytes, particularly polymer analytes, to pass through a detection zone in sequence, or in other words, so that monomers pass a detection zone one at a time, or in single file, (ii) compatibility with a translocating means (if one is used), that is, whatever method is used to drive an analyte through a nanopore, such as an electric field, and optionally, (iii) suppression of fluorescent signals within the lumen, or bore, of the nanopore. In some embodiments, nanopores used in connection with the methods and devices of the invention are provided in the form of arrays, such as an array of clusters of nanopores, which may be disposed regularly on a planar surface. In some embodiments, clusters are each in a separate resolution limited area so that optical signals from nanopores of different clusters are distinguishable by the optical detection system employed, but optical signals from nanopores within the same cluster cannot necessarily be assigned to a specific nanopore within such cluster by the optical system employed.

Nanopores may be fabricated in a variety of materials including but not limited to, silicon nitride ($Si_3N_4$), silicon dioxide ($SiO_2$), and the like. The fabrication and operation of nanopores for analytical applications, such as DNA sequencing, are disclosed in the following exemplary references that are incorporated by reference: Russell, U.S. Pat. No. 6,528,258; Feier, U.S. Pat. No. 4,161,690; Ling, U.S. Pat. No. 7,678,562; Hu et al, U.S. Pat. No. 7,397,232; Golovchenko et al, U.S. Pat. No. 6,464,842; Chu et al, U.S. Pat. No. 5,798,042; Sauer et al, U.S. Pat. No. 7,001,792; Su et al, U.S. Pat. No. 7,744,816; Church et al, U.S. Pat. No. 5,795,782; Bayley et al, U.S. Pat. No. 6,426,231; Akeson et al, U.S. Pat. No. 7,189,503; Bayley et al, U.S. Pat. No. 6,916,665; Akeson et al, U.S. Pat. No. 6,267,872; Meller et al, U.S. patent publication 2009/0029477; Howorka et al, International patent publication WO2009/007743; Brown et al, International patent publication WO2011/067559; Meller et al, International patent publication WO2009/020682; Polonsky et al, International patent publication WO2008/092760; Van der Zaag et al, International patent publication WO2010/007537; Yan et al, Nano Letters, 5(6): 1129-1134 (2005); Iqbal et al, Nature Nanotechnology, 2: 243-248 (2007); Wanunu et al, Nano Letters, 7(6): 1580-1585 (2007); Dekker, Nature Nanotechnology, 2: 209-215 (2007); Storm et al, Nature Materials, 2: 537-540 (2003); Wu et al, Electrophoresis, 29(13): 2754-2759 (2008); Nakane et al, Electrophoresis, 23: 2592-2601 (2002); Zhe et al, J. Micromech. Microeng., 17: 304-313 (2007); Henriquez et al, The Analyst, 129: 478-482 (2004); Jagtiani et al, J. Micromech. Microeng., 16: 1530-1539 (2006); Nakane et al, J. Phys. Condens. Matter, 15 R1365-R1393 (2003); DeBlois et al, Rev. Sci. Instruments, 41(7): 909-916 (1970); Clarke et al, Nature Nanotechnology, 4(4): 265-270 (2009); Bayley et al, U.S. patent publication 2003/0215881; and the like.

Briefly, in some embodiments, a 1-50 nm channel or aperture is formed through a substrate, usually a planar substrate, such as a membrane, through which an analyte, such as single stranded DNA, is induced to translocate. The solid-state approach of generating nanopores offers robustness and durability as well as the ability to tune the size and shape of the nanopore, the ability to fabricate high-density arrays of nanopores on a wafer scale, superior mechanical, chemical and thermal characteristics compared with lipid-based systems, and the possibility of integrating with electronic or optical readout techniques. Biological nanopores on the other hand provide reproducible narrow bores, or lumens, especially in the 1-10 nanometer range, as well as techniques for tailoring the physical and/or chemical properties of the nanopore and for directly or indirectly attaching groups or elements, such as fluorescent labels, which may be FRET donors or acceptors, by conventional protein engineering methods. Protein nanopores typically rely on delicate lipid bilayers for mechanical support, and the fabrication of solid-state nanopores with precise dimensions remains challenging. In some embodiments, solid-state nanopores may be combined with a biological nanopore to form a so-called "hybrid" nanopore that overcomes some of these shortcomings, thereby providing the precision of a biological pore protein with the stability of a solid state nanopore. For optical read out techniques a hybrid nanopore provides a precise location of the nanopore which simplifies the data acquisition greatly.

In some embodiments, arrays of clusters of nanopores of the invention may be used with a method for analyzing one or more polymer analytes comprising the following steps: (a) translocating a polymer analyte through a nanopore having a bore and an exit, the polymer analyte comprising a sequence of monomers, wherein substantially each monomer is labeled with a fluorescent label such that fluorescent labels of adjacent monomers are in a quenched state by self-quenching one another outside of the nanopore and fluorescent labels are in a sterically constrained state and incapable of generating a detectable fluorescent signal inside of the nanopore; (b) exciting each fluorescent label at the exit of the nanopore as it transitions from a sterically constrained state to a quenched state so that a fluorescent signal is generated which is indicative of the monomer to which it is attached; (c) detecting the fluorescent signal to identify the monomer. As used herein, "substantially every", "substantially all", or like terms, in reference to labeling monomers, particularly nucleotides, acknowledges that chemical labeling procedures may not result in complete labeling of every monomer; to the extent practicable, the terms comprehend that labeling reactions in connection with the invention are continued to completion; in some embodiments, such completed labeling reactions include labeling at least fifty percent of the monomers; in other embodiments, such labeling reactions include labeling at least eighty percent of the monomers; in other embodiments, such labeling reactions include labeling at least ninety-five percent of the monomers; in other embodiments, such labeling reactions include labeling at least ninety-nine percent of the monomers.

In another embodiment, arrays of clusters of nanopores of the invention may be used with a method for analyzing one or more polymer analytes comprising the following steps: (a) attaching a fluorescent label substantially every monomer of one or more polymer analytes such that fluorescent labels of adjacent monomers are in a quenched state, (b) translocating the polymer analytes through nanopores so that monomers of each polymer analyte traverses the nanopore in single file and wherein each nanopore has a bore and an exit, the bore sterically constraining the fluorescent labels in a constrained state so that no fluorescent signal is generated therefrom inside the bore; (c) exciting during a transition interval each fluorescent label at the exit of the nanopore as each fluorescent label transitions from a sterically constrained state to a quenched state, thereby generating a fluorescent signal that is indicative of the monomer to which it is attached; (c) detecting the fluorescent signal to identify the monomer.

In another embodiment, arrays of clusters of nanopores of the invention may be used with a device for analyzing one or more labeled polymer analytes, such as a device for determining a nucleotide sequence of one or more labeled polynucleotide analytes, such device comprising the following elements: (a) a solid phase membrane separating a first chamber and a second chamber, the solid phase membrane having at least one nanopore fluidly connecting the first chamber and the second chamber through a bore or lumen, the bore or lumen having a cross-sectional dimension such that labels of a labeled polymer translocating therethrough are sterically constrained so that detectable signals are not generated, and so that the labels of adjacent monomers of the labeled polymer are self-quenching; (b) an excitation source for exciting each label when it exits the nanopore and enters the second chamber so that a signal is generated indicative of a monomer to which the label is attached; and (c) a detector for collecting at least a portion of the signal generated by each excited label; and (d) identifying the monomer to which the excited label is attached by the collected signal.

In some embodiments, methods and devices of the invention comprise a solid phase membrane, such as a SiN membrane, having an array of apertures therethrough providing communication between a first chamber and a second chamber (also sometimes referred to as a "cis chamber" and a "trans chamber") and supporting a lipid bilayer on a surface facing the second, or trans, chamber. In some embodiments, diameters of the aperture in such a solid phase membrane may be in the range of 10 to 200 nm, or in the range of 20 to 100 nm. In some embodiments, such solid phase membranes further include protein nanopores inserted into the lipid bilayer in regions where such bilayer spans the apertures on the surface facing the trans chamber. In some embodiments, such protein nanopores are inserted from the cis side of the solid phase membrane using techniques described herein. In some embodiments, such protein nanopores have a structure identical to, or similar to, α-hemolysin in that it comprises a barrel, or bore, along an axis and at one end has a "cap" structure and at the other end has a "stem" structure (using the terminology from Song et al, Science, 274: 1859-1866 (1996)). In some embodiments using such protein nanopores, insertion into the lipid bilayer results in the protein nanopore being oriented so that its cap structure is exposed to the cis chamber and its stem structure is exposed to the trans chamber.

In some embodiments, methods and devices of the invention comprise droplet interface bilayers, either as single droplets or as arrays droplets, for example, as disclosed in Bayley et al, U.S. patent publication 2014/0356289; Huang et al, Nature Nanotechnology, 10.1038/nnano.2015.189. [Epub ahead of print]; or like reference, which are hereby incorporated by reference. Briefly, protein nanopores (1.2 nM) are placed in a 200-350 nl droplet (for example, 1.32 M KCl, 8.8 mM HEPES, 0.4 mM EDTA, pH 7.0 (αHL) or 8.0 (MspA), and incubated in, for example, 3 mM 1,2-diphytanoyl-sn-glycero-3-phosphocholine (DPhPC) in hexadecane to form a lipid monolayer coating. A droplet may then be transferred by pipetting onto a coverslip in a measurement chamber, for example, that permits application of voltages to move analytes and optical detection, for example, by TIRF. The coverslip may be spin coated (3,000 r.p.m., 30 s) with a thin layer (~200 nm) of agarose (0.66 M CaCl2, 8.8 mM HEPES, pH 7.0 (αHL)/8.0 (MspA)) and subsequently incubated with 3 mM DPhPC in hexadecane. On contact with the monolayer on the agarose, a lipid coated droplet spontaneously forms a droplet interface bilayer. A ground electrode (Ag/AgCl) may be inserted into the droplet, with a corresponding active electrode (Ag/AgCl) in the substrate agarose. Voltage protocols may be applied with a patch clamp amplifier (for example, Axopatch 200B, Molecular Devices). Nanopores present in the droplet spontaneously insert into the droplet interface bilayer, and the ion flux may be detected both electrically and/or optically (for example, by way of an ion-sensitive dye, such as Fluo-8, or the like).

In some embodiments, the solid phase membrane may be treated with a low energy ion beam to bleach its autofluorescence, e.g. as described in Huber et al, U.S. patent publication 2013/0203050, which is incorporated herein by reference.

FIGS. 2A-2C are diagrams of embodiments of hybrid biosensors. A nanometer sized hole (2102) is drilled into a solid-state substrate, or solid phase membrane, (2103) which separates two chambers, or compartments cis (2101) and trans (2107). A protein biosensor (e.g a protein nanopore) (2104) attached to a charged polymer (2105), such as a single stranded DNA, is embedded into the solid-state nanohole by electrophoretic transport. In FIG. 1C the protein biosensor is inserted. In a nanometer sized hole which surface has a hydrophobic coating (2106) and a lipid layer (2109) attached thereto. A nanopore may have two sides, or orifices. One side is referred to as the "cis" side and faces the (−) negative electrode or a negatively charged buffer/ion compartment or solution. The other side is referred to as the "trans" side and faces the (+) electrode or a positively charged buffer/ion compartment or solution. A biological polymer, such as a labeled nucleic acid molecule or polymer can be pulled or driven through the pore by an electric field applied through the nanopore, e.g., entering on the cis side of the nanopore and exiting on the trans side of the nanopore. In accordance with the invention, such nanopores may be arranged in an array of clusters of such nanopores.

Figure 2D:
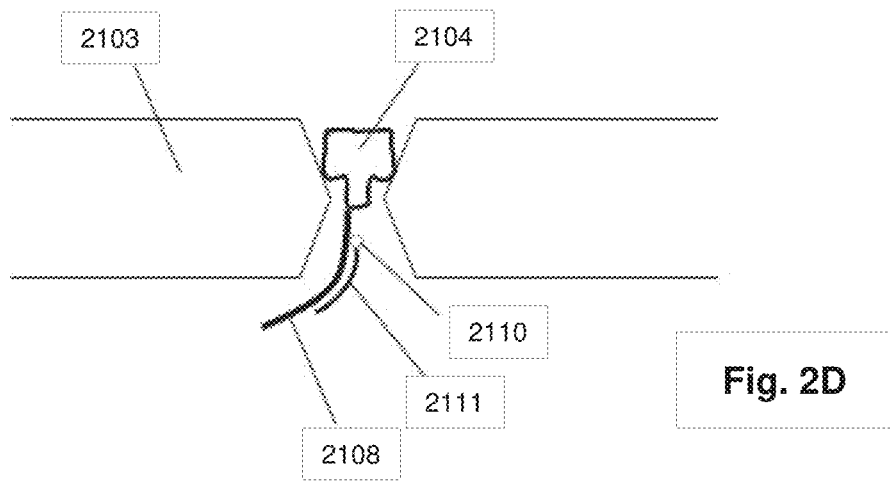
FIG. 2D illustrate an embodiment of the nanopore of the invention with positioning of a member of a FRET pair using oligonucleotide hybridization.
Figure 2E:
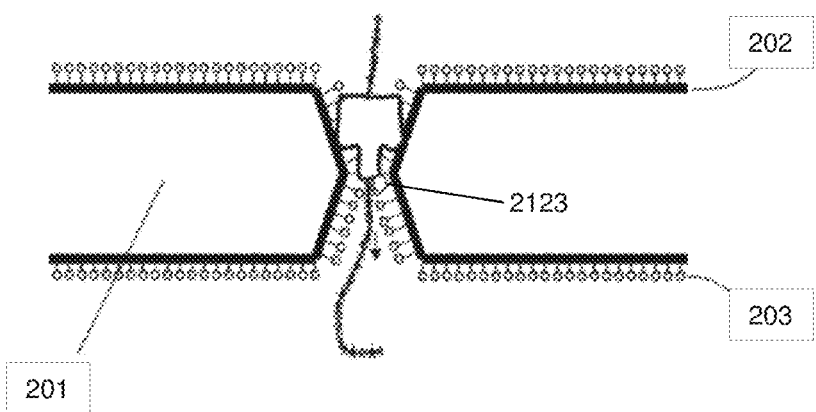
FIG. 2E illustrates one embodiment of a hybrid nanopore where the surface of the solid state membrane (201) coated with a hydrophobic layer (202) to which a lipid layer is adhered (203). The lipids forms a gigaohm seal with the inserted nanopore protein.

FIG. 2D shows an embodiment of a hybrid nanopore wherein protein nanopore (2104) inserted into an aperture drilled in a solid state membrane (2103). Attached to the protein nanopore (2104) is an oligonucleotide (2108) to which a complementary secondary oligonucleotide (2111) is hybridized. In some embodiments, secondary oligonucleotide (2111) has one or more second members of a FRET pair (2110) attached to it. Alternatively, a member of a FRET pair may be directly attached to an amino acid of a protein nanopore, e.g. label (2123) of FIG. 2E. For example, a hemolysin subunit may be modified by conventional genetic engineering techniques to substitute a cysteine for a suitably located amino acid adjacent to the exit of the nanopore, e.g. the threonine 129. An oligonucleotide or members of a FRET pair may be attached via the thio group of the cysteine using conventional linker chemistries, e.g. Hermanson (cited above).

In some embodiments, the present invention may employ hybrid nanopores in clusters, particularly for optical-based nanopore sequencing of polynucleotides. Such nanopores comprise a solid-state orifice, or aperture, into which a protein biosensor, such as a protein nanopore, is stably inserted. A protein nanopore (e.g. alpha hemolysin) may be attached to a charged polymer (e.g. double stranded DNA) which in an applied electric field may be used to guide a protein nanopore into an aperture in a solid-state membrane. In some embodiments, the aperture in the solid-state substrate is selected to be slightly smaller than the protein, thereby preventing it from translocating through the aperture. Instead, the protein will be embedded into the solid-state orifice. The solid-state substrate can be modified to generate active sites on the surface that allow the covalent attachment of the plugged-in protein biosensor resulting in a stable hybrid biosensor.

The polymer attachment site in the protein nanopore can be generated by protein engineering e.g. a mutant protein can be constructed that will allow the specific binding of the polymer. As an example, a cysteine residue may be inserted at the desired position of the protein. The cysteine can either replace a natural occurring amino acid or can be incorporated as an addition amino acid. Care must be taken not to disrupt the biological function of the protein. The terminal primary amine group of a polymer (i.e. DNA) is then activated using a hetero-bifunctional crosslinker (e.g. SMCC). Subsequently, the activated polymer is covalently attached to the cysteine residue of the protein biosensor. In some embodiments, the attachment of the polymer to the biosensor is reversible. By implementing a cleavable crosslinker, an easily breakable chemical bond (e.g. an S—S bond) is introduced and the charged polymer may be removed after insertion of the biosensor into the solid-state aperture.

For someone skilled in the art it is obvious that a wide variety of different approaches for covalent or non-covalent attachment methods of a charged polymer to the protein nanopore are possible and the above described approach merely serves as an example. The skilled artisan will also realize that a variety of different polymers may be used as a drag force, including, but not limited to, single or double stranded DNA, polyethyleneglycol (PEG), polyvinylpyrrolidone (PVP), poly-L-lysine, linear polysaccharides etc. It is also obvious that these polymers may exhibit either a negative (−) or positive (+) charge at a given pH and that the polarity of the electric field may be adjusted accordingly to pull the polymer-biosensor complex into a solid-state aperture.

In some embodiments, a donor fluorophore is attached to the protein nanopore. This complex is then inserted into a solid-state aperture or nanohole (for example, 3-10 nm in diameter) by applying an electric field across the solid state nanohole, or aperture, until the protein nanopore is transported into the solid-state nanohole to form a hybrid nanopore. The formation of the hybrid nanopore can be verified by (a) the inserted protein nanopore causing a drop in current based on a partial blockage of the solid-state nanohole and by (b) the optical detection of the donor fluorophore.

Once stable hybrid nanopores have formed single stranded, fluorescently labeled (or acceptor labeled) DNA is added to the cis chamber (the chamber with the (+) electrode). The applied electric field forces the negatively charged ssDNA to translocate through the hybrid nanopore during which the labeled nucleotides get in close vicinity of the donor fluorophore.

Solid state, or synthetic, nanopores may be preprared in a variety of ways, as exemplified in the references cited above. In some embodiments a helium ion microscope may be used to drill the synthetic nanopores in a variety of materials, e.g. as disclosed by Yang et al, Nanotechnolgy, 22: 285310 (2011), which is incorporated herein by reference. A chip that supports one or more regions of a thin-film material, e.g. silicon nitride, that has been processed to be a free-standing membrane is introduced to the helium ion microscope (HIM) chamber. HIM motor controls are used to bring a free-standing membrane into the path of the ion beam while the microscope is set for low magnification. Beam parameters including focus and stigmation are adjusted at a region adjacent to the free-standing membrane, but on the solid substrate. Once the parameters have been properly fixed, the chip position is moved such that the free-standing membrane region is centered on the ion beam scan region and the beam is blanked. The HIM field of view is set to a dimension (in μm) that is sufficient to contain the entire anticipated nanopore pattern and sufficient to be useful in future optical readout (i.e. dependent on optical magnification, camera resolution, etc.). The ion beam is then rastered once through the entire field of view at a pixel dwell time that results in a total ion dose sufficient to remove all or most of the membrane autofluorescence. The field of view is then set to the proper value (smaller than that used above) to perform lithographically-defined milling of either a single nanopore or an array of nanopores. The pixel dwell time of the pattern is set to result in nanopores of one or more predetermined diameters, determined through the use of a calibration sample prior to sample processing. This entire process is repeated for each desired region on a single chip and/or for each chip introduced into the HIM chamber.

In some embodiments, the solid-state substrate may be modified to generate active sites on the surface that allow the covalent attachment of the plugged in protein biosensor or to modify the surface properties in a way to make it more suitable for a given application. Such modifications may be of covalent or non-covalent nature. A covalent surface modification includes a silanization step where an organosilane compound binds to silanol groups on the solid surface. For instance, the alkoxy groups of an alkoxysilane are hydrolyzed to form silanol-containing species. Reaction of these silanes involves four steps. Initially, hydrolysis of the labile groups occurs. Condensation to oligomers follows. The oligomers then hydrogen bond with hydroxyl groups of the substrate. Finally, during drying or curing, a covalent linkage is formed with the substrate with concomitant loss of water. For covalent attachment organosilanes with active side groups may be employed. Such side groups consist of, but are not limited to epoxy side chain, aldehydes, isocyanates, isothiocyanates, azides or alkynes (click chemistry) to name a few. For someone skilled in the art it is obvious that multiple ways of covalently attaching a protein to a surface are possible. For instance, certain side groups on an organosilane may need to be activated before being capable of binding a protein (e.g. primary amines or carboxyl side groups activated with an N-hydroxysuccinimidester).

Another way of attaching a protein to the solid surface may be achieved through affinity binding by having one affinity partner attached to the protein and the second affinity partner being located on the solid surface. Such affinity pairs consist of the group of, but are not limited to biotin-strepavidin, antigen-antibody and aptamers and the corresponding target molecules. In a preferred embodiment the surface modification of the solid state nanopore includes treatment with an organosilane that renders the surface hydrophobic. Such organosilanes include but are not limited to, alkanesilanes (e.g. octadecyldimethylchlorosilane) or modified alkanesilanes such as fluorinated alkanesilanes with an alkane chain length of 5 to 30 carbons. The hydrophobic surface may then treated with a dilute solution of a lipid in pentane. After drying of the solvent and immersing the surface in an aqueous solution the lipid will spontaneously form a layer on the surface.

In some embodiments, a layer of lipid on the solid surface may be beneficial for the formation of a hybrid nanopore. The lipid layer on the solid phase may reduce the leak current between protein and solid state nanopore and it may increase the stability of the inserted protein pore. Combining a low capacitance solid substrate as well as a lipid coating of said substrate may render the hybrid nanopore system amenable to an electrical readout based on current fluctuations generated by translocation of DNA through the hybrid nanopore. To achieve electrical read out with such a system a means of decreasing the translocation speed of unmodified DNA must be combined with a lipid coated hybrid nanopore. Molecular motors such as polymerases or helicases may be combined with a hybrid nanopore and effectively reduce the translocation speed of DNA through the hybrid nanopore. The lipids used for coating the surface are from the group of sphingolipids, phospholipids or sterols. A method and/or system for sequencing a biological polymer or molecule (e.g., a nucleic acid) may include exciting one or more donor labels attached to a pore or nanopore. A biological polymer may be translocated through the pore or nanopore, where a monomer of the biological polymer is labeled with one or more acceptor labels. Energy may be transferred from the excited donor label to the acceptor label of the monomer as, after the labeled monomer passes through, exits or enters the pore or nanopore. Energy emitted by the acceptor label as a result of the energy transfer may be detected, where the energy emitted by the acceptor label may correspond to or be associated with a single or particular monomer (e.g., a nucleotide) of a biological polymer. The sequence of the biological polymer may then be deduced or sequenced based on the detection of the emitted energy from the monomer acceptor label which allows for the identification of the labeled monomer. A pore, nanopore, channel or passage, e.g., an ion permeable pore, nanopore, channel or passage may be utilized in the systems and methods described herein.

In some embodiments, a nanopore may have one or more labels attached. In some embodiments, the label is a member of a Forster Resonance Energy Transfer (FRET) pair. Such labels may comprise organic fluorophores, chemiluminescent labels, quantum dots, metallic nanoparticles and/or fluorescent proteins. The nucleic acid may have one distinct label per nucleotide. The labels attached to the nucleotides may be selected from the group consisting of organic fluorophores, chemiluminescent labels, quantum dots, metallic nanoparticles and fluorescent proteins. The label attachment site in the pore protein can be generated by protein engineering e.g. a mutant protein can be constructed that will allow the specific binding of the label. As an example, a cysteine residue may be inserted at the desired position of the protein which inserts a thiol (SH) group that can be used to attach a label. The cysteine can either replace a natural occurring amino acid or can be incorporated as an addition amino acid. A malemeide-activated label is then covalently attached to the thiol residue of the protein nanopore. In a preferred embodiment the attachment of the label to the protein nanopore or the label on the nucleic acid is reversible. By implementing a cleavable crosslinker, an easily breakable chemical bond (e.g. an S—S bond or a pH labile bond) is introduced and the label may be removed when the corresponding conditions are met.

A nanopore, or pore, may be labeled with one or more donor labels. For example, the cis side or surface and/or trans side or surface of the nanopore may be labeled with one or more donor labels. The label may be attached to the base of a pore or nanopore or to another portion or monomer making up the nanopore or pore A label may be attached to a portion of the membrane or substrate through which a nanopore spans or to a linker or other molecule attached to the membrane, substrate or nanopore. The nanopore or pore label may be positioned or attached on the nanopore, substrate or membrane such that the pore label can come into proximity with an acceptor label of a biological polymer, e.g., a nucleic acid, which is translocated through the pore. The donor labels may have the same or different emission or absorption spectra. The labeling of a pore structure may be achieved via covalent or non-covalent interactions.

A donor label (also sometimes referred to herein as a "pore label") may be placed as close as possible to the aperture (for example, at the exit) of a nanopore without causing an occlusion that impairs translocation of a nucleic acid through the nanopore. A pore label may have a variety of suitable properties and/or characteristics. For example, a pore label may have energy absorption properties meeting particular requirements. A pore label may have a large radiation energy absorption cross-section, ranging, for example, from about 0 to 1000 nm or from about 200 to 500 nm. A pore label may absorb radiation within a specific energy range that is higher than the energy absorption of the nucleic acid label, such as an acceptor label. The absorption energy of the pore label may be tuned with respect to the absorption energy of a nucleic acid label in order to control the distance at which energy transfer may occur between the two labels. A pore label may be stable and functional for at least $10^6$ to $10^9$ excitation and energy transfer cycles.

In some embodiments, a device for analyzing polymers each having optical labels attached to a sequence of monomers may comprise the following elements: (a) a nanopore array in a solid phase membrane separating a first chamber and a second chamber, wherein nanopores of the nanopore array each provide fluid communication between the first chamber and the second chamber and are arranged in clusters such that each different cluster of nanopores is disposed within a different resolution limited area and such that each cluster comprises a number of nanopores that is either greater than one or is a random variable with an average value greater than zero; (b) a polymer translocating system for moving polymers in the first chamber to the second chamber through the nanopores of the nanopore array; and (c) a detection system for collecting optical signals generated by optical labels attached to polymers whenever an optical label exits a nanopore within a resolution limited area.

Labels for Nanopores and Analytes

In some embodiments, a nanopore may be labeled with one or more quantum dots. In particular, in some embodiments, one or more quantum dots may be attached to a nanopore, or attached to a solid phase support adjacent to (and within a FRET distance of an entrance or exit of a nanopore), and employed as donors in FRET reactions with acceptors on analytes. Such uses of quantum dots are well known and are described widely in the scientific and patent literature, such as, in U.S. Pat. Nos. 6,252,303; 6,855,551; 7,235,361; and the like, which are incorporated herein by reference.

One example of a Quantum dot which may be utilized as a pore label is a CdTe quantum dot which can be synthesized in an aqueous solution. A CdTe quantum dot may be functionalized with a nucleophilic group such as primary amines, thiols or functional groups such as carboxylic acids. A CdTe quantum dot may include a mercaptopropionic acid capping ligand, which has a carboxylic acid functional group that may be utilized to covalently link a quantum dot to a primary amine on the exterior of a protein pore. The cross-linking reaction may be accomplished using standard cross-linking reagents (homo-bifunctional as well as hetero-bifunctional) which are known to those having ordinary skill in the art of bioconjugation. Care may be taken to ensure that the modifications do not impair or substantially impair the translocation of a nucleic acid through the nanopore. This may be achieved by varying the length of the employed crosslinker molecule used to attach the donor label to the nanopore.

For example, the primary amine of the lysine residue 131 of the natural alpha hemolysin protein (Song, L. et al., Science 274, (1996): 1859-1866) may be used to covalently bind carboxy modified CdTe Quantum dots via 1-Ethyl-3-[3-dimethylaminopropyl]carbodiimide hydrochloride/N-hydroxysulfosuccinimide (EDC/NHS) coupling chemistry. Alternatively, amino acid 129 (threonine) may be exchanged into cysteine. Since there is no other cysteine residue in the natural alpha hemolysin protein the thiol side group of the newly inserted cysteine may be used to covalently attach other chemical moieties.

A variety of methods, mechanisms and/or routes for attaching one or more pore labels to a pore protein may be utilized. A pore protein may be genetically engineered in a manner that introduces amino acids with known properties or various functional groups to the natural protein sequence. Such a modification of a naturally occurring protein sequence may be advantageous for the bioconjugation of Quantum dots to the pore protein. For example, the introduction of a cysteine residue would introduce a thiol group that would allow for the direct binding of a Quantum dot, such as a CdTe quantum dot, to a pore protein. Also, the introduction of a Lysin residue would introduce a primary amine for binding a Quantum dot. The introduction of glutamic acid or aspartic acid would introduce a carboxylic acid moiety for binding a Quantum dot. These groups are amenable for bioconjugation with a Quantum dot using either homo- or hetero-bifunctional crosslinker molecules. Such modifications to pore proteins aimed at the introduction of functional groups for bioconjugation are known to those having ordinary skill in the art. Care should be taken to ensure that the modifications do not impair or substantially impair the translocation of a nucleic acid through the nanopore.

The nanopore label can be attached to a protein nanopore before or after insertion of said nanopore into a lipid bilayer. Where a label is attached before insertion into a lipid bilayer, care may be taken to label the base of the nanopore and avoid random labeling of the pore protein. This can be achieved by genetic engineering of the pore protein to allow site specific attachment of the pore label, as discussed below. An advantage of this approach is the bulk production of labeled nanopores. Alternatively, a labeling reaction of a pre-inserted nanopore may ensure site-specific attachment of the label to the base (trans-side) of the nanopore without genetically engineering the pore protein.

A biological polymer, e.g., a nucleic acid molecule or polymer, may be labeled with one or more acceptor labels. For a nucleic acid molecule, each of the four nucleotides or building blocks of a nucleic acid molecule may be labeled with an acceptor label thereby creating a labeled (e.g., fluorescent) counterpart to each naturally occurring nucleotide. The acceptor label may be in the form of an energy accepting molecule which can be attached to one or more nucleotides on a portion or on the entire strand of a converted nucleic acid.

A variety of methods may be utilized to label the monomers or nucleotides of a nucleic acid molecule or polymer. A labeled nucleotide may be incorporated into a nucleic acid during synthesis of a new nucleic acid using the original sample as a template ("labeling by synthesis"). For example, the labeling of nucleic acid may be achieved via PCR, whole genome amplification, rolling circle amplification, primer extension or the like or via various combinations and extensions of the above methods known to persons having ordinary skill in the art.

Labeling of a nucleic acid may be achieved by replicating the nucleic acid in the presence of a modified nucleotide analog having a label, which leads to the incorporation of that label into the newly generated nucleic acid. The labeling process can also be achieved by incorporating a nucleotide analog with a functional group that can be used to covalently attach an energy accepting moiety in a secondary labeling step. Such replication can be accomplished by whole genome amplification (Zhang, L. et al., Proc. Natl. Acad. Sci. USA 89 (1992): 5847) or strand displacement amplification such as rolling circle amplification, nick translation, transcription, reverse transcription, primer extension and polymerase chain reaction (PCR), degenerate oligonucleotide primer PCR (DOP-PCR) (Telenius, H. et al., Genomics 13 (1992): 718-725) or combinations of the above methods.

A label may comprise a reactive group such as a nucleophile (amines, thiols etc.). Such nucleophiles, which are not present in natural nucleic acids, can then be used to attach fluorescent labels via amine or thiol reactive chemistry such as NHS esters, maleimides, epoxy rings, isocyanates etc. Such nucleophile reactive fluorescent dyes (i.e. NHS-dyes) are readily commercially available from different sources. An advantage of labeling a nucleic acid with small nucleophiles lies in the high efficiency of incorporation of such labeled nucleotides when a "labeling by synthesis" approach is used. Bulky fluorescently labeled nucleic acid building blocks may be poorly incorporated by polymerases due to steric hindrance of the labels during the polymerization process into newly synthesized DNA.

In some embodiments, DNA can be directly chemically modified without polymerase mediated incorporation of labeled nucleotides. One example of a modification includes cis-platinum containing dyes that modify Guanine bases at their N7 position (Hoevel, T. et al., Bio Techniques 27 (1999): 1064-1067). Another example includes the modifying of pyrimidines with hydroxylamine at the C6 position which leads to 6-hydroxylamino derivatives. The resulting amine groups can be further modified with amine reactive dyes (e.g. NHS-Cy5). Yet another example are azide or alkyne modified nucleotides which are readily incorporated by polymerases (Gierlich et al., Chem. Eur. J., 2007, 13, 9486-0404). The alkyne or azide modified polynucleotide is subsequently labeled with an azide or alkyne modified fluorophore following well established click chemistry protocols.

As mentioned above, in some embodiments, DNA may be labeled using "click chemistry," e.g. using commercially available kits (such as "Click-It" from Life Technologies, Carlsbad, Calif.). Click chemistry in general refers to a synthetic process in which two molecules are linked together by a highly efficient chemical reaction, one which is essentially irreversible, in which the yield is nearly 100%, and which produces few or no reaction byproducts. More recently, the meaning has come to refer to the cyclization reaction of a substituted alkyne with a substituted azide to form a 1,2,3-triazole bearing the two substituents. When catalyzed by copper at room temperature the reaction is known as the Huisgen cycloaddition, and it fully satisfies the requirements for click chemistry in that no other chemical functionality on the two molecules is affected during the reaction. Thus the coupling reaction has found broad application in bioconjugate chemistry, for example, in dye labeling of DNA or proteins, where many amine, hydroxy, or thiol groups may be found. The key requirement is that an alkyne group and an azide can easily be introduced into the molecules to be coupled. For example, in the coupling of a fluorescent dye to a DNA oligonucleotide, the azide group is typically introduced synthetically into the dye, while the alkyne group is incorporated into the DNA during oligonucleotide synthesis. Upon mixing in the presence of Cu+ the two components are quickly coupled to form the triazole, in this case bearing the oligonucleotide as one substituent and the dye as the other. Another more recent advance provides the alkyne component within a strained ring structure. In this case the reaction with an azide does not require the copper catalyst, being driven by release of the ring strain energy as the triazole is formed. This is better known as the copper-free click reaction. Guidance for applying click chemistry to methods of the invention may be found in the following references which are incorporated by reference: Rostovtsev V V. Green L G; Fokin, Valery V, Sharpless K B (2002). "A Stepwise Huisgen Cycloaddition Process: Copper(I)-Catalyzed Regioselective "Ligation" of Andes and Terminal Alkynes". *Angewandte Chemie International Edition* 41 (14): 2596-2599. Moses J E and Moorhouse A D (2007). "The growing applications of click chemistry". *Chem. Soc. Rev.* 36 (8): 1249-1262.

Whenever two or more mutually quenching dyes are used, such dyes may be attached to DNA using orthogonal attachment chemistries. For example, NHS esters can be used to react very specifically with primary amines or maleimides will react with thiol groups. Either primary amines ($NH_2$) or thiol (SH) modified nucleotides are commercially available. These relatively small modifications are readily incorporated in a polymerase mediated DNA synthesis and can be used for subsequent labeling reactions using either NHS or maleimide modified dyes. Guidance for selecting and using such orthogonal linker chemistries may be found in Hermanson (cited above).

Additional orthogonal attachment chemistries for typical attachment positions include Huisgen-type cycloaddition for a copper-catalyzed reaction and an uncatalyzed reaction; alkene plus nitrile oxide cycloaddition, e.g. as disclosed in Gutsmiedl et al, Org. Lett., 11: 2405-2408 (2009); Diels-Alder cycloaddition, e.g. disclosed in Seelig et al, Tetrahedron Lett., 38: 7729-7732 (1997); carbonyl ligation, e.g. as disclosed in Casi et al, J. Am. Chem. Soc., 134: 5887-5892 (2012); Shao et al J. Am. Chem. Soc., 117: 3893-3899 (1995); Rideout, Science, 233: 561-563 (1986); Michael addition, e.g. disclosed in Brinkley, Bioconjugate Chemistry, 3: 2-13 (1992); native chemical ligation, e.g. disclosed in Schuler et al, Bioconjugate Chemistry, 13: 1039-1043 (2002); Dawson et al, Science, 266: 776-779 (1994); or amide formation via an active ester, e.g. disclosed in Hermanson (cited above).

A nucleic acid molecule may be directly modified with N-Bromosuccinimide which upon reacting with the nucleic acid will result in 5-Bromocystein, 8-Bromoadenine and 8-Bromoguanine. The modified nucleotides can be further reacted with di-amine nucleophiles. The remaining nucleophile can then be reacted with an amine reactive dye (e.g. NHS-dye) (Hermanson G, in Bioconjugate Techniques, cited above).

A combination of 1, 2, 3 or 4 nucleotides in a nucleic acid strand may be exchanged with their labeled counterpart. The various combinations of labeled nucleotides can be sequenced in parallel, e.g., labeling a source nucleic acid or DNA with combinations of 2 labeled nucleotides in addition to the four single labeled samples, which will result in a total of 10 differently labeled sample nucleic acid molecules or DNAs (G, A, T, C, GA, GT, GC, AT, AC, TC). The resulting sequence pattern may allow for a more accurate sequence alignment due to overlapping nucleotide positions in the redundant sequence read-out. In some embodiments, a polymer, such as a polynucleotide or polypeptide, may be labeled with a single fluorescent label attached to a single kind of monomer, for example, every T (or substantially every T) of a polynucleotide is labeled with a fluorescent label, e.g. a cyanine dye. In such embodiments, a collection, or sequence, of fluorescent signals from the polymer may form a signature or fingerprint for the particular polymer. In some such embodiments, such fingerprints may or may not provide enough information for a sequence of monomers to be determined.

In some embodiments, a feature of the invention is the labeling of substantially all monomers of a polymer analyte with fluorescent dyes or labels that are members of a mutually quenching set. The use of the term "substantially all" in reference to labeling polymer analytes is to acknowledge that chemical and enzymatic labeling techniques are typically less than 100 percent efficient. In some embodiments, "substantially all" means at least 80 percent of all monomer have fluorescent labels attached. In other embodiments, "substantially all" means at least 90 percent of all monomer have fluorescent labels attached. In other embodiments, "substantially all" means at least 95 percent of all monomer have fluorescent labels attached.

A method for sequencing a polymer, such as a nucleic acid molecule includes providing a nanopore or pore protein (or a synthetic pore) inserted in a membrane or membrane like structure or other substrate. The base or other portion of the pore may be modified with one or more pore labels. The base may refer to the Trans side of the pore. Optionally, the Cis and/or Trans side of the pore may be modified with one or more pore labels. Nucleic acid polymers to be analyzed or sequenced may be used as a template for producing a labeled version of the nucleic acid polymer, in which one of the four nucleotides or up to all four nucleotides in the resulting polymer is/are replaced with the nucleotide's labeled analogue(s). An electric field is applied to the nanopore which forces the labeled nucleic acid polymer through the nanopore, while an external monochromatic or other light source may be used to illuminate the nanopore, thereby exciting the pore label. As, after or before labeled nucleotides of the nucleic acid pass through, exit or enter the nanopore, energy is transferred from the pore label to a nucleotide label, which results in emission of lower energy radiation. The nucleotide label radiation is then detected by a confocal microscope setup or other optical detection system or light microscopy system capable of single molecule detection known to people having ordinary skill in the art. Examples of such detection systems include but are not limited to confocal microscopy, epifluorescent microscopy and total internal reflection fluorescent (TIRF) microscopy. Other polymers (e.g., proteins and polymers other than nucleic acids) having labeled monomers may also be sequenced according to the methods described herein. In some embodiments, fluorescent labels or donor molecules are excited in a TIRF system with an evanescent wave, sometimes referred to herein as "evanescent wave excitation."

Energy may be transferred from a pore or nanopore donor label (e.g., a Quantum Dot) to an acceptor label on a polymer (e.g., a nucleic acid) when an acceptor label of an acceptor labeled monomer (e.g., nucleotide) of the polymer interacts with the donor label as, after or before the labeled monomer exits, enters or passes through a nanopore. For example, the donor label may be positioned on or attached to the nanopore on the cis or trans side or surface of the nanopore such that the interaction or energy transfer between the donor label and acceptor label does not take place until the labeled monomer exits the nanopore and comes into the vicinity or proximity of the donor label outside of the nanopore channel or opening. As a result, interaction between the labels, energy transfer from the donor label to the acceptor label, emission of energy from the acceptor label and/or measurement or detection of an emission of energy from the acceptor label may take place outside of the passage, channel or opening running through the nanopore, e.g., within a cis or trans chamber on the cis or trans sides of a nanopore. The measurement or detection of the energy emitted from the acceptor label of a monomer may be utilized to identify the monomer.

The nanopore label may be positioned outside of the passage, channel or opening of the nanopore such that the label may be visible or exposed to facilitate excitation or illumination of the label. The interaction and energy transfer between a donor label and accepter label and the emission of energy from the acceptor label as a result of the energy transfer may take place outside of the passage, channel or opening of the nanopore. This may facilitate ease and accuracy of the detection or measurement of energy or light emission from the acceptor label, e.g., via an optical detection or measurement device.

A donor label may be attached in various manners and/or at various sites on a nanopore. For example, a donor label may be directly or indirectly attached or connected to a portion or unit of the nanopore. Alternatively, a donor label may be positioned adjacent to a nanopore.

Each acceptor labeled monomer (e.g., nucleotide) of a polymer (e.g., nucleic acid) can interact sequentially with a donor label positioned on or next to or attached directly or indirectly to the exit of a nanopore or channel through which the polymer is translocated. The interaction between the donor and acceptor labels may take place outside of the nanopore channel or opening, e.g., after the acceptor labeled monomer exits the nanopore or before the monomer enters the nanopore. The interaction may take place within or partially within the nanopore channel or opening, e.g., while the acceptor labeled monomer passes through, enters or exits the nanopore.

When one of the four nucleotides of a nucleic acid is labeled, the time dependent signal arising from the single nucleotide label emission is converted into a sequence corresponding to the positions of the labeled nucleotide in the nucleic acid sequence. The process is then repeated for each of the four nucleotides in separate samples and the four partial sequences are then aligned to assemble an entire nucleic acid sequence.

When multi-color labeled nucleic acid (DNA) sequences are analyzed, the energy transfer from one or more donor labels to each of the four distinct acceptor labels that may exist on a nucleic acid molecule may result in light emission at four distinct wavelengths or colors (each associated with one of the four nucleotides) which allows for a direct sequence read-out.

Translocation Speed

A major obstacle associated with nanopore based sequencing approaches is the high translocation velocity of nucleic acid through a nanopore (~500,000-1,000,000 nucleotides/sec) which doesn't allow for direct sequence readout due to the limited bandwidth of the recording equipment. A way of slowing down the nucleic acid translocation with two different nanopore proteins was recently shown by Cherf et al. (Nat Biotechnol. 2012 Feb. 14; 30(4):344-8) and Manrao et al. (Nat Biotechnol. 2012 Mar. 25; 30(4):349-53) and are incorporated herein by reference. Both groups used a DNA polymerase to synthesize a complementary strand from a target template which resulted in the step-wise translocation of the template DNA through the nanopore. Hence, the synthesis speed of the nucleic acid polymerase (10-500 nucleotides/sec) determined the translocation speed of the DNA and since it's roughly 3-4 orders of magnitude slower than direct nucleic acid translocation the analysis of single nucleotides became feasible. However, the polymerase-aided translocation requires significant sample preparation to generate a binding site for the polymerase and the nucleic acid synthesis has to be blocked in bulk and can only start once the nucleic acid-polymerase complex is captured by the nanopore protein. This results in a rather complex set-up which might prevent the implementation in a commercial setting. Furthermore, fluctuation in polymerase synthesis reactions such as a stalled polymerization as well as the dissociation of the polymerase from the nucleic acid may hamper the sequence read-out resulting in a high error rate and reduced read-length, respectively. In some embodiments, a target nucleic acid is enzymatically copied by incorporating fluorescent modified nucleotides. The resulting labeled nucleic acid has an increased nominal diameter which results in a decreased translocation velocity when pulled through a nanopore. The preferred translocation rate for optical sequencing lies in the range of 1-1000 nucleotides per second with a more preferred range of 200-800 nucleotides per second and a most preferred translocation rate of 200-600 nucleotides per second.

Alternatively, translocation speed of a polynucleotide, especially a single stranded polynucleotide, may be controlled by employing a nanopore dimensioned so that adducts and/or labels, e.g. organic dyes attached to bases, inhibit but do not prevent polynucleotide translocation. A translocation speed may be selected by attaching labels and/or adducts at a predetermined density. Such labels and/or adducts may have regular spaced attachments, e.g. every third nucleotide or the like, or they may have random, or pseudorandom attachments, e.g. every C may be labeled. In some embodiments, a selected number of different nucleotides may be labeled, e.g. every A and C, or every A and G, or every A and T, or every C, or the like, that results in an average translocation speed. Such average speed may be decreased by attaching adducts to unlabeled nucleotides. Adducts include any molecule, usually and organic molecule, that may be attached to a nucleotide using conventional chemistries. Typically adducts have a molecular weight in the same range as common organic dyes, e.g. fluorescein, Cy3, or the like. Adducts may or may not be capable of generating signals, that is, serving as a label. In some embodiments, adducts and/or labels are attached to bases of nucleotides. In other embodiments, labels and/or adducts may be attached to linkages between nucleosides in a polynucleotide. In one aspect, a method of controlling translocation velocity of a single stranded polynucleotide through a nanopore comprises the step of attaching adducts to the polynucleotide at a density, wherein translocation velocity of the single stranded polynucleotide monotonically decreases with a larger number of adducts attached, or with the density of adducts attached. In some embodiments, not every kind of nucleotide of a polynucleotide is labeled. For example, four different sets of a polynucleotide may be produced where nucleotides of each set are labeled with the same molecule, e.g. a fluorescent organic dye acceptor, but in each set a different kind of nucleotide will be labeled. Thus, in set 1 only A's may be labeled; in set 2 only C's may be labeled; in set 3 only G's may be labeled; and so on. After such labeling, the four sets of polynucleotides may then be analyzed separately in accordance with the invention and a nucleotide sequence of the polynucleotide determined from the data generated in the four analysis. In such embodiments, and similar embodiments, e.g. two labels are used, where some of the nucleotides of a polynucleotide are not labeled, translocation speed through a nanopore will be affected by the distribution of label along the polynucleotide. To prevent such variability in translocation speed, in some embodiments, nucleotides that are not labeled with an acceptor or donor for generating signals to determine nucleotide sequence, may be modified by attaching a non-signal-producing adduct that has substantially the same effect on translocation speed as the signal-producing labels.

Nanopore Sequencing with Mutually Quenching Fluorescent Labels

The invention relates to the use of nanopores and fluorescent quenching to sequentially identify monomers of polymer analytes. Such analysis of polymer analytes may be carried out on single polymer analytes or on pluralities of polymer analytes in parallel at the same time. In some embodiments, monomers are labeled with fluorescent labels that are capable of at least three states while attached to a target polymer: (i) A quenched state wherein fluorescence of an attached fluorescent label is quenched by a fluorescent label on an immediately adjacent monomer; for example, a fluorescent label attached to a polymer in accordance with the invention is quenched when the labeled polymer is free in an aqueous solution. (ii) A sterically constrained state wherein a labeled polymer is translocating through a nanopore such that the free-solution movements or alignments of an attached fluorescent label is disrupted or limited so that there is little or no detectable signal generated from the fluorescent label. (iii) A transition state wherein a fluorescent label attached to a polymer transitions from the sterically constrained state to the quenched state as the fluorescent label exits the nanopore (during a "transition interval") while the polymer translocates through the nanopore. In part, the invention is an application of the discovery that during the transition interval a fluorescent label is capable of generating a detectable fluorescent signal. Without the intention of being limited by any theory underlying this discovery, it is believed that the fluorescent signal generated during the transition interval is due to a freely rotatable dipole. In both, the sterically constrained state as well as the quenched state the dipoles are limited in their rotational freedom thereby reducing or limiting the number of emitted photons. In some embodiments, the polymer is a polynucleotide, usually a single stranded polynucleotide, such as, DNA or RNA, but especially DNA. In some embodiments, the invention includes a method for determining a nucleotide sequence of a polynucleotide by recording signals generated by attached fluorescent labels as they exit a nanopore one at a time as a polynucleotide translocates the nanopore. Upon exit, each attached fluorescent label transitions during a transition interval from a constrained state in the nanopore to a quenched state on the polynucleotide in free solution. As mentioned above, during this transition interval or period the fluorescent label is capable of emitting a detectable fluorescent signal indicative of the nucleotide it is attached to.

In some embodiments, a nucleotide sequence of a target polynucleotide is determined by carrying out four separate reactions in which copies of the target polynucleotide have each of its four different kinds of nucleotide (A, C, G and T) labeled with a single fluorescent label. In a variant of such embodiments, a nucleotide sequence of a target polynucleotide is determined by carrying out four separate reactions in which copies of the target polynucleotide have each of its four different kinds of nucleotide (A, C, G and T) labeled with one fluorescent label while at the same time the other nucleotides on the same target polynucleotide are labeled with a second fluorescent label. For example, if a first fluorescent label is attached to A's of the target polynucleotide in a first reaction, then a second fluorescent label is attached to C's, G's and T's (i.e. to the "not-A" nucleotides) of the target polynucleotides in the first reaction. Likewise, in continuance of the example, in a second reaction, the first label is attached to C's of the target polynucleotide and the second fluorescent label is attached to A's, G's and T's (i.e. to the "not-C" nucleotides) of the target polynucleotide. And so on, for nucleotides G and T.

The same labeling scheme may be expressed in terms of conventional terminology for subsets of nucleotide types; thus, in the above example, in a first reaction, a first fluorescent label is attached to A's and a second fluorescent label is attached to B's; in a second reaction, a first fluorescent label is attached to C's and a second fluorescent label is attached to D's; in a third reaction, a first fluorescent label is attached to G's and a second fluorescent label is attached to H's; and in a fourth reaction, a first fluorescent label is attached to T's and a second fluorescent label is attached to V's.

In some embodiments, a feature of the invention is the labeling of substantially all monomers of a polymer analytes with fluorescent dyes or labels that are members of a mutually quenching set. Such sets of fluorescent dyes have the following properties: (i) each member quenches fluorescence of every member (for example, by FRET or by static or contact mechanisms), and (ii) each member generates a distinct fluorescent signal when excited and when in a non-quenching state. That is, if a mutually quenching set consists of two dyes, D1 and D2, then (i) D1 is self-quenched (e.g. by contact quenching with another D1 molecule) and it is quenched by D2 (e.g. by contact quenching) and (ii) D2 is self-quenched (e.g. by contact quenching with another D2 molecule) and it is quenched by D1 (e.g. by contact quenching). Guidance for selecting fluorescent dyes or labels for mutually quenching sets may be found in the following references, which are incorporated herein by reference: Johansson, Methods in Molecular Biology, 335: 17-29 (2006); Marras et al, Nucleic Acids Research, 30: e122 (2002); and the like. Exemplary mutually quenching sets of fluorescent dyes, or labels, may be selected from rhodamine dyes, fluorescein dyes and cyanine dyes. In one embodiment, a mutually quenching set may comprise the rhodamine dye, TAMRA, and the fluorescein dye, FAM. In another embodiment, mutually quenching sets of fluorescent dyes may be formed by selecting two or more dyes from the group consisting of Oregon Green 488, Fluorescein-EX, fluorescein isothiocyanate, Rhodamine Red-X, Lissamine rhodamine B, Calcein, Fluorescein, Rhodamine, one or more BODIPY dyes, Texas Red, Oregon Green 514, and one or more Alexa Fluors. Respresentative BODIPY dyes include BODIPY FL, BODIPY R6G, BODIPY TMR, BODIPY 581/591, BODIPY TR, BODIPY 630/650 and BODIPY 650/665. Representative Alexa Fluors include Alexa Fluor 350, 405, 430, 488, 500, 514, 532, 546, 555, 568, 594, 610, 633, 635, 647, 660, 680, 700, 750 and 790.

In some embodiments, fluorescent labels are members of a FRET pair. A FRET pair generally is one or more FRET donors and one or more FRET acceptors where each donor is capable of a FRET reaction with each acceptor. In one aspect, this means that the donors of the FRET pair have an emission spectrum that substantially overlaps the absorption spectrum of the acceptors. In another aspect, the transition dipole of the donor and the acceptor have to be aligned in a way that allows efficient energy transfer. In some aspects, the invention in part is based on the discovery and appreciation of a fluorescence, particularly, FRET suppressing property of nanopores and the application of this property to enable detection of labeled polymers translocating through a nanopore. It is believed, although the invention is not intended to be limited thereby, that a nanopore may be selected with a bore dimensioned so that a FRET pair label cannot orient to engage in a FRET interaction while translocating through the nanopore. The dipoles of the labels of the polynucleoide in the bore of the nanopore are constrained in their rotational freedom based on the limited diameter of the nanopore. This reduction in dipole alignment with the alignment of the corresponding FRET pair attached to the nanopore limits the FRET efficiency dramatically. Labeled polynucleotides can engage in a FRET interaction after exiting the nanopore at which point the FRET acceptor or donor on the polymer (e.g. polynucleotide) regains rotational freedom which allows for a FRET event.

A wide range of embodiments of the above may be implemented depending on the type of analytes being detected, the types of donors and acceptors employed, the physical arrangement of the nanopores, donors and acceptors, whether analytes are labeled with donors or with acceptors, and the like. In one embodiment, analytes measured by the invention are acceptor-labeled polymers, especially acceptor-labeled polynucleotides. In one species of the latter embodiment, different nucleotides of a polynucleotide analyte are labeled with one or more different kinds of acceptors, so that a nucleotide sequence of the polynucleotide may be determined from measuring FRET signals generated as it translocates through a nanopore. In another embodiment, analytes measured by the invention are donor-labeled polymers, especially donor-labeled polynucleotides. The sequence of the polynucleotide may be determined from measuring FRET signals as it translocates through a nanopore. In yet another embodiment of the present invention, at least one of the four nucleotides of a polynucleotide analyte is labeled with a member of a FRET pair. The positions of the labeled nucleotides in the polynucleotide are determined by translocating the labeled polynucleotide through a labeled nanopore and measuring FRET events. By labeling the remaining nucleotides of the same polynucleotide sample and subsequently translocating said samples through a labeled nanopore, sub-sequences of the polynucleotide are generated. Such sub-sequences can be re-aligned resulting in a full sequence of the polynucleotide.

Figure 3:
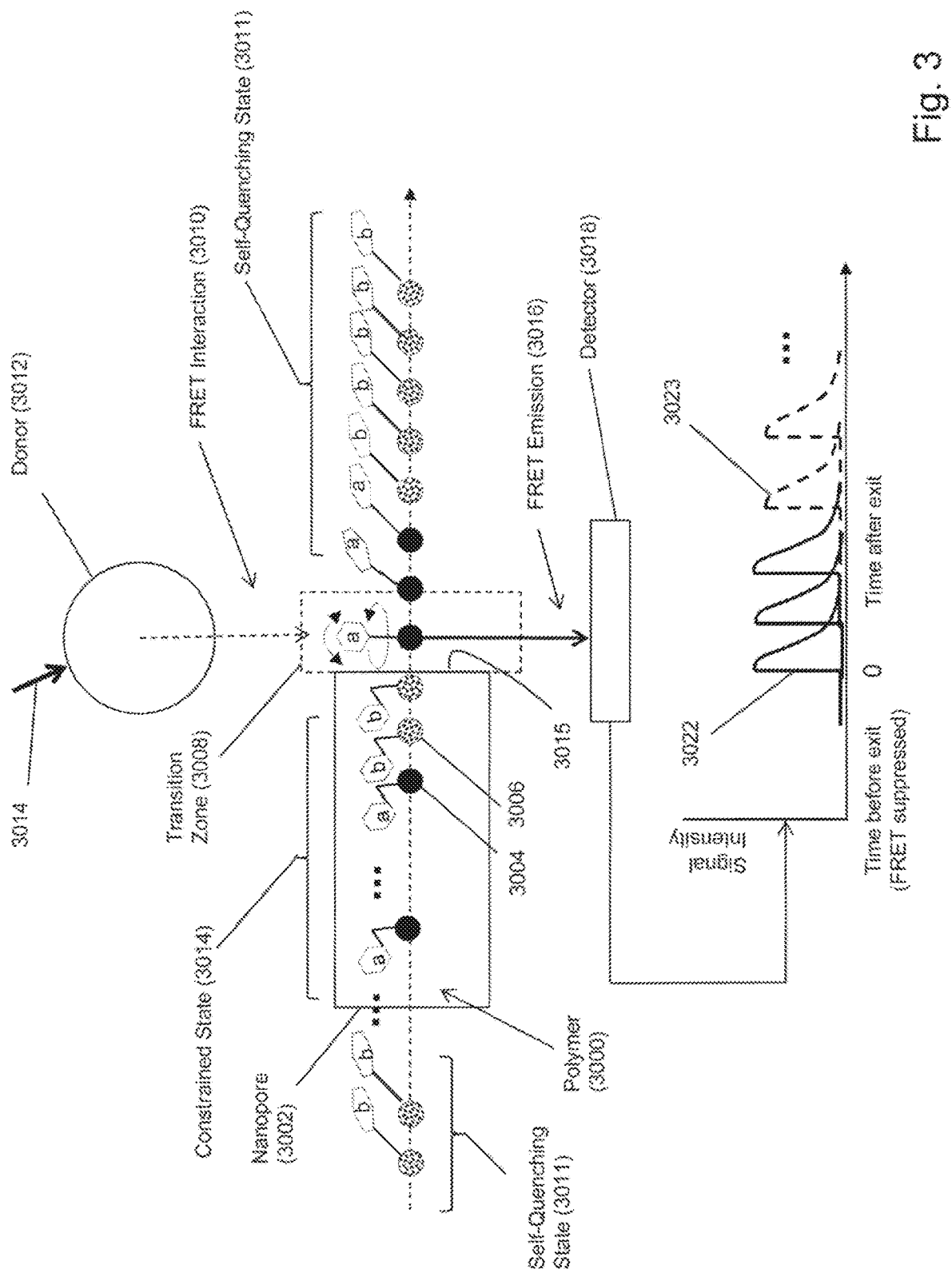
FIG. 3 illustrates a nanopore device and method for use with the present invention.

Some of the above aspects and embodiments of the invention are illustrated diagrammatically in FIG. 3. Polymer analyte (3000), such as a polynucleotide, is driven, e.g. electrophoretically, through nanopore (3002), which constrains the conformation of polymer (3000) so that its monomeric units translocate through the nanopore in the same order as their primary sequence in the polymer. In the embodiment shown in FIG. 3, fluorescent labels are assumed to be members of FRET pairs, but this is not intended to limit the present invention; fluorescent labels may also include fluorescent labels that are directly excited, for example with a laser emitting at an appropriate wavelength, to generate a fluorescent signal.

As mentioned above, whenever an acceptor-labeled monomeric unit is within the bore of nanopore (3002), FRET interactions between such acceptors and the donors of its FRET pair are suppressed because acceptors are in a constrained state (3014). Such suppression typically means that no detectable FRET signal is produced even if such acceptors are within a FRET distance of a donor, for example, due to unfavorable orientation of the acceptor and donor dipoles. On the other hand, when an acceptor-labeled monomeric unit emerges from the bore of, or exits, the nanopore into transition zone (3008), FRET interaction (3010) occurs and FRET emission (3016) is produced and detected by detector (3018) until the acceptor enters a self-quenching state (3011) with an adjacent acceptor and as the distance between the acceptor and donor increases with the movement of polymer (3000) out of FRET interaction distance. Signal (3022) is produced by a single acceptor as it moves through transition zone (3008). Transition zone (3008), which is a spatial region immediately adjacent to exit (3015) of nanopore (3002), is defined by several factors, including the speed of the translocation of polymer (3000) through nanopore (3002), the vibrational and rotational mobility of the fluorescent labels, the physiochemical nature of the fluorescent labels, and the like. In FIG. 3, only one type of monomeric unit, illustrated as solid circles (3004) carries a first fluorescent label (designated as "a"); the rest of the monomeric units, illustrated as speckled circles (3006), carry a second fluorescent label (designated as "b"). In this embodiment, first fluorescent labels quench adjacent first fluorescent labels and adjacent second fluorescent labels; likewise, second fluorescent labels quench adjacent first fluorescent labels and adjacent second fluorescent labels; moreover, the first and second fluorescent labels generate FRET signals that are distinguishable from one another, for example, recorded signal (3022) for label "a" and recorded signal (3023) for label "b" in FIG. 3, so that each fluorescent label (and hence, monomer) may be identified by a signal detected by detector (3018).

In some embodiments, a nanopore is hybrid nanopore comprising a protein nanopore inserted into a pore of a solid phase membrane, as described above. In hybrid nanopores, a first member of a FRET pair may be attached directly to the protein nanopore, or alternatively, directly to the solid phase membrane using conventional linking chemistries, such as "click" chemistries, e.g. Kolb et al, Angew. Chem. Int. Ed., 4): 2004-2021 (2001), or the like. In one embodiment, a first member of a FRET pair is attached directly or indirectly to the protein nanopore, for example, as discussed in reference to FIG. 2D. In another embodiment, the first member of the FRET pair is a donor and a quantum dot. Quantum dots are typically much larger than acceptors, especially acceptors that are organic dyes, which typically have molecular weights in the range of from 200 to 2000 daltons.

In one embodiment, the present invention may be used in a method for analyzing one or more polymer analytes, such as determining a nucleotide sequence of a polynucleotide, which comprises the following steps: (a) translocating polymer analytes through nanopores of a nanopore array, each nanopore having a bore and an exit, each polymer analyte comprising a sequence of monomers, wherein substantially each monomer is labeled with a fluorescent label such that fluorescent labels of adjacent monomers are in a quenched state by self-quenching one another outside of the nanopore and fluorescent labels are in a sterically constrained state and incapable of generating a detectable fluorescent signal inside of the nanopore; (b) exciting each fluorescent label at the exit of the nanopores as it transitions from a sterically constrained state to a quenched state so that a fluorescent signal is generated which is indicative of the monomer to which it is attached; (c) detecting the fluorescent signal to identify the monomer, wherein the nanopore array is an array of clusters. As used herein, "substantially every", "substantially all", or like terms, in reference to labeling monomers, particularly nucleotides, acknowledges that chemical labeling procedures are rarely complete; to the extent practicable, the terms comprehend that labeling reactions in connection with the invention are continued to completion; in some embodiments, such completed labeling reactions include labeling at least fifty percent of the monomers; in other embodiments, such labeling reactions include labeling at least eighty percent of the monomers; in other embodiments, such labeling reactions include labeling at least ninety-five percent of the monomers; in other embodiments, such labeling reactions include labeling at least ninety-nine percent of the monomers.

In another embodiment the invention is directed to a device for analyzing one or more labeled polymer analytes, such as a device for determining a nucleotide sequence of one or more labeled polynucleotide analytes, such device comprising the following elements: (a) a solid phase membrane separating a first chamber and a second chamber, the solid phase membrane having an array of nanopores each fluidly connecting the first chamber and the second chamber through a bore or lumen, the bore or lumen having a cross-sectional dimension such that labels of a labeled polymer translocating therethrough are sterically constrained so that detectable signals are not generated, and so that the labels of adjacent monomers of the labeled polymer are self-quenching; (b) an excitation source for exciting each label when it exits each nanopore and enters the second chamber so that a signal is generated indicative of a monomer to which the label is attached; and (c) a detector for collecting at least a portion of the signal generated by each excited label; and (d) identifying the monomer to which the excited label is attached by the collected signal whenever emitted from a sequence-able nanopore; and wherein the array of nanopores is an array of clusters of nanopores.

In another embodiment, the invention is directed to a system for analyzing polymers comprising a polymer comprising monomers that are substantially all labeled with a mutually quenching dye set and a nanopore device for sequentially detecting optical signals from the dyes of the mutually quenching dye set which are attached to the polymer. Such an embodiment for determining a sequence of a polynucleotide may comprise the following elements: (a) a solid phase membrane separating a first chamber and a second chamber, the solid phase membrane having an array of apertures each connecting the first chamber and the second chamber, and having a hydrophobic coating on at least one surface; (b) a lipid layer disposed on the hydrophobic coating; (c) protein nanopores immobilized in the apertures, the protein nanopores each having a bore with an exit, and the protein nanopores interacting with the lipid layer to form a seal with the solid phase membrane in the apertures so that fluid communication between the first chamber and the second chamber occurs solely through the bore of the protein nanopore, and the protein nanopores each being cross-sectionally dimensioned so that nucleotides of the polynucleotide pass through the exit of the bore in sequence and so that fluorescent labels attached to the polynucleotide are sterically constrained; and (d) a first member of the FRET pair attached to the solid phase membrane or the protein nanopore, so that whenever nucleotides of the polynucleotide emerge from the bore, a plurality of the nucleotides are within a FRET distance of the first member of the FRET pair; and wherein the array of apertures is an array of clusters of apertures.

Arrays of Zero Mode Waveguides for Sequence Analysis

Arrays of zero mode waveguides have been developed for analyzing in parallel populations of single molecules each undergoing a sequence of reactions that generate a corresponding sequence of optical signals, e.g. Levene et al, Science, 299: 682-686 (2003); Korlach et al, Proc. Natl. Acad. Sci., 105(4): 1176-1181 (2008). This approach has been applied to develop a high-throughput DNA sequencing instrument, Eid et al, Science, 323: 133-138 (2009). Such applications are further disclosed in the following U.S. patents which are incorporated herein by reference: U.S. Pat. Nos. 7,302,146; 7,476,503; 7,906,284; 8,709,725; and the like. Typically, in arrays of zero mode waveguides used for these applications, the waveguides are regularly spaced with an inter-waveguide distance sufficiently large that optical signals from adjacent waveguides can be optically distinguished and do not substantially affect the values of collected signals. Such spacing is usually greater than the wavelength of the light comprising the optical signals, so that, as described above for nanopore arrays, the full capabilities of nano-engineering techniques for close placement of features is not employed. Accordingly, the efficiency of such methods may be improved by employing arrays of clusters in accordance with the invention.

In some embodiments, an improved method of performing multiple chemical reactions involving a plurality of reaction samples may be performed with the following steps: (a) providing an array of nanowells; (b) placing the plurality of reaction samples comprising labeled reactants into the nanowells of the array, wherein a separate reaction sample is placed into a different nanowell in the array; (c) subjecting the array to conditions suitable for formation of products of the chemical reactions; and (d) detecting the formation of the products with an optical system operationally associated therewith, and wherein nanowells of the array are arranged in clusters such that each different cluster of nanowells is disposed within a different resolution limited area and such that an average number of nanowells in each cluster is greater than zero. In some embodiments, nanowells of an array each comprise an optical confinement and/or a zero mode waveguide, as described in U.S. Pat. No. 7,302,146.

In some embodiments, an improved method of sequencing a plurality of target nucleic acid molecules may be performed by the following steps: (a) providing an array of nanowells, wherein nanowells of the array are arranged in clusters such that each different cluster of nanowells is disposed within a different resolution limited area and such that an average number of nanowells in each cluster is greater than zero, and wherein each nanowell provide an effective observation volume that permits observation of individual molecules; and an optical system operatively coupled to the nanowells that detects signals from the effective observation volume of the nanowells; (b) mixing in the nanowells the plurality of target nucleic acid molecules, primers complementary to the target nucleic acid molecules, polymerization enzymes, and more than one type of nucleotides or nucleotide analogs to be incorporated into a plurality of nascent nucleotide strands, each strand being complementary to a respective target nucleic acid molecule; (c) subjecting the mixture of step (b) to a polymerization reaction under conditions suitable for formation of the nascent nucleotide strands by template-directed polymerization of the nucleotides or nucleotide analogs; (d) illuminating the nanowells with an incident light beam; and (e) identifying the nucleotides or the nucleotide analogs incorporated into the each nascent nucleotide strand. As above, in some embodiments, nanowells of an array each comprise an optical confinement and/or a zero mode waveguide, as described in U.S. Pat. No. 7,302,146.

Definitions

"Cluster" in reference to an array of nanostructures means a distribution of a plurality of groups or collections of nanostructures wherein each group occupies a separate area of the array and wherein intra-group nanostructure-to-nanostructure distances are much less than inter-group nanostructure-to-nanostructure distances. In some embodiments, such a distribution is substantially planar; that is, if nanostructures are spaced relative to a surface, the curvature of such surface is small in the proximity of a cluster. In some embodiments, a cluster of nanostructures is encompassed by a resolution limited area, such that nanostructures of different clusters are in different resolution limited areas. The number of nanostructures within a cluster may vary widely. In some embodiments, nanostructure arrays may be fabricated with a predetermined number of nanostructures within each cluster of the array. For example, clusters of an array may each have a plurality of nanostructures; in other embodiments, clusters of an array may each have from 1 to 100 nanostructures; in other embodiments, clusters may each have from 2 to 50 nanostructures; in other embodiments, clusters may each have from 2 to 16 nanostructures. In some embodiments, each cluster of an array may have the same number of nanostructures. In other embodiments, the number of nanostructures within a cluster may be a random variable, such that an average, or expected, number, and possibly its variance, characterizes clusters within an array. In some embodiments, clusters of nanostructures are clusters of nanopores; in other embodiments, clusters of nanostructures are clusters of nanowells, including, but not limited to, nanowells that are zero mode waveguides. In some embodiments, for example, where nanostructures comprise protein nanopores, a random variable representing the number of nanopores in a cluster may be a Poisson random variable whose average value depends on the concentration of protein nanopores in a solution used to load an array of apertures.

"FRET" or "Förster, or fluorescence, resonant energy transfer" means a non-radiative dipole-dipole energy transfer mechanism from an excited donor fluorophore to an acceptor fluorophore in a ground state. The rate of energy transfer in a FRET interaction depends on the extent of spectral overlap of the emission spectrum of the donor with the absorption spectrum of the acceptor, the quantum yield of the donor, the relative orientation of the donor and acceptor transition dipoles, and the distance between the donor and acceptor molecules, Lakowitz, Principles of Fluorescence Spectroscopy, Third Edition (Springer, 2006). FRET interactions of particular interest are those which result a portion of the energy being transferred to an acceptor, in turn, being emitted by the acceptor as a photon, with a frequency lower than that of the light exciting its donor (i.e. a "FRET signal"). "FRET distance" means a distance between a FRET donor and a FRET acceptor over which a FRET interaction can take place and a detectable FRET signal produced by the FRET acceptor.

"Kit" refers to any delivery system for delivering materials or reagents for carrying out a method of the invention. In the context of reaction assays, such delivery systems include systems that allow for the storage, transport, or delivery of reaction reagents (e.g., fluorescent labels, such as mutually quenching fluorescent labels, fluorescent label linking agents, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second or more containers contain mutually quenching fluorescent labels.

"Microfluidics" device or "nanofluidics" device, used interchangeably herein, each means an integrated system for capturing, moving, mixing, dispensing or analyzing small volumes of fluid, including samples (which, in turn, may contain or comprise cellular or molecular analytes of interest), reagents, diluants, buffers, or the like. Generally, reference to "microfluidics" and "nanofluidics" denotes different scales in the size of devices and volumes of fluids handled. In some embodiments, features of a microfluidic device have cross-sectional dimensions of less than a few hundred square micrometers and have passages, or channels, with capillary dimensions, e.g. having maximal cross-sectional dimensions of from about 500 µm to about 0.1 µm. In some embodiments, microfluidics devices have volume capacities in the range of from 1 µL to a few nL, e.g. 10-100 nL. Dimensions of corresponding features, or structures, in nanofluidics devices are typically from 1 to 3 orders of magnitude less than those for microfluidics devices. One skilled in the art would know from the circumstances of a particular application which dimensionality would be pertinent. In some embodiments, microfluidic or nanofluidic devices have one or more chambers, ports, and channels that are interconnected and in fluid communication and that are designed for carrying out one or more analytical reactions or processes, either alone or in cooperation with an appliance or instrument that provides support functions, such as sample introduction, fluid and/or reagent driving means, such as positive or negative pressure, acoustical energy, or the like, temperature control, detection systems, data collection and/or integration systems, and the like. In some embodiments, microfluidics and nanofluidics devices may further include valves, pumps, filters and specialized functional coatings on interior walls, e.g. to prevent adsorption of sample components or reactants, facilitate reagent movement by electroosmosis, or the like. Such devices may be fabricated in or as a solid substrate, which may be glass, plastic, or other solid polymeric materials, and may have a planar format for ease of detecting and monitoring sample and reagent movement, especially via optical or electrochemical methods. In some embodiments, such devices are disposable after a single use. In some embodiments, microfluidic and nanofluidic devices include devices that form and control the movement, mixing, dispensing and analysis of droplets, such as, aqueous droplets immersed in an immiscible fluid, such as a light oil. The fabrication and operation of microfluidics and nanofluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437; Cao, "Nanostructures & Nanomaterials: Synthesis, Properties & Applications," (Imperial College Press, London, 2004); Haeberle et al, LabChip, 7: 1094-1110 (2007); Cheng et al, Biochip Technology (CRC Press, 2001); and the like.

"Nanopore" means any opening positioned in a substrate that allows the passage of analytes through the substrate in a predetermined or discernable order, or in the case of polymer analytes, passage of their monomeric units through the substrate in a predetermined or discernible order. In the latter case, a predetermined or discernible order may be the primary sequence of monomeric units in the polymer. Examples of nanopores include proteinaceous or protein based nanopores, synthetic or solid state nanopores, and hybrid nanopores comprising a solid state nanopore having a protein nanopore embedded therein. A nanopore may have an inner diameter of 1-10 nm or 1-5 nm or 1-3 nm. Examples of protein nanopores include but are not limited to, alpha-hemolysin, voltage-dependent mitochondrial porin (VDAC), OmpF, OmpC, MspA and LamB (maltoporin), e.g. disclosed in Rhee, M. et al., Trends in Biotechnology, 25(4) (2007): 174-181; Bayley et al (cited above); Gundlach et al, U.S. patent publication 2012/0055792; and the like, which are incorporated herein by reference. Any protein pore that allows the translocation of single nucleic acid molecules may be employed. A nanopore protein may be labeled at a specific site on the exterior of the pore, or at a specific site on the exterior of one or more monomer units making up the pore forming protein. Pore proteins are chosen from a group of proteins such as, but not limited to, alpha-hemolysin, MspA, voltage-dependent mitochondrial porin (VDAC), Anthrax porin, OmpF, OmpC and LamB (maltoporin). Integration of the pore protein into the solid state hole is accomplished by attaching a charged polymer to the pore protein. After applying an electric field the charged complex is electrophoretically pulled into the solid state hole. A synthetic nanopore, or solid-state nanopore, may be created in various forms of solid substrates, examples of which include but are not limited to silicones (e.g. Si3N4, SiO2), metals, metal oxides (e.g. Al2O3) plastics, glass, semiconductor material, and combinations thereof. A synthetic nanopore may be more stable than a biological protein pore positioned in a lipid bilayer membrane. A synthetic nanopore may also be created by using a carbon nanotube embedded in a suitable substrate such as but not limited to polymerized epoxy. Carbon nanotubes can have uniform and well-defined chemical and structural properties. Various sized carbon nanotubes can be obtained, ranging from one to hundreds of nanometers. The surface charge of a carbon nanotube is known to be about zero, and as a result, electrophoretic transport of a nucleic acid through the nanopore becomes simple and predictable (Ito, T. et al., Chem. Commun. 12 (2003): 1482-83). The substrate surface of a synthetic nanopore may be chemically modified to allow for covalent attachment of the protein pore or to render the surface properties suitable for optical nanopore sequencing. Such surface modifications can be covalent or non-covalent. Most covalent modification include an organosilane deposition for which the most common protocols are described: 1) Deposition from aqueous alcohol. This is the most facile method for preparing silylated surfaces. A 95% ethanol-5% water solution is adjusted to pH 4.5-5.5 with acetic acid. Silane is added with stirring to yield a 2% final concentration. After hydrolysis and silanol group formation the substrate is added for 2-5 min. After rinsed free of excess materials by dipping briefly in ethanol. Cure of the silane layer is for 5-10 min at 110 degrees Celsius. 2) Vapor Phase Deposition. Silanes can be applied to substrates under dry aprotic conditions by chemical vapor deposition methods. These methods favor monolayer deposition. In closed chamber designs, substrates are heated to sufficient temperature to achieve 5 mm vapor pressure. Alternatively, vacuum can be applied until silane evaporation is observed. 3) Spin-on deposition. Spin-on applications can be made under hydrolytic conditions which favor maximum functionalization and polylayer deposition or dry conditions which favor monolayer deposition. In some embodiments, single nanopores are employed with methods of the invention. In other embodiments, a plurality of nanopores are employed. In some of the latter embodiments, a plurality of nanopores is employed as an array of nanopores, usually disposed in a planar substrate, such as a solid phase membrane. Nanopores of a nanopore array may be spaced regularly, for example, in a rectilinear pattern, or may be spaced randomly. In a preferred embodiment, nanopores are spaced regularly in a rectilinear pattern in a planar solid phase substrate.

"Nanostructure" (used interchangeably with "nanoscale structure" and "nanoscale feature") means a structure that has at least one dimension within a range of a few nanometers to several hundred nanometers, for example, from 1 to 1000 nanometers. In some applications, such range is from 2 to 500 nanometers; in other applications, such range is from 3 to 500 nanometers. The shape and geometry of nanostructures may vary widely and include, but are not limited to, nanopores, nanowells, nanoparticles, and any other convenient shapes particularly suitable for carrying out sequences of reactions. In some embodiments, nanostructures may be protein nanopores operationally associated with a solid phase membrane. Some nanostructures, such as, nanopores and nanowells, may be formed in a larger common substrate, such as a solid phase membrane, or other solid, to form arrays of nanopores or nanowells. Nanostructures of particular interest are those capable of supporting or containing a chemical, physical (e.g. FRET), enzymatic and/or binding reaction or a sequence of such reactions. In some embodiments, a nanostructure, such as a nanowell, encloses a volume that is less than one nanoliter (10×-9 liter), less than one picoliter, or less than one femtoliter. In other embodiments, each of the individual nanowells provides a volume that is less than 1000 zeptoliters, 100 zeptoliters, 80 zeptoliters, or less than 50 zeptoliters, or less than 1 zeptoliter, or even less than 100 yactoliters. In some embodiments, nanowells comprise zero mode waveguides.

"Peptide," "peptide fragment," "polypeptide," "oligopeptide," or "fragment" in reference to a peptide are used synonymously herein and refer to a compound made up of a single unbranched chain of amino acid residues linked by peptide bonds. Amino acids in a peptide or polypeptide may be derivatized with various moieties, including but not limited to, polyethylene glycol, dyes, biotin, haptens, or like moieties. The number of amino acid residues in a protein or polypeptide or peptide may vary widely; however, in some embodiments, protein or polypeptides or peptides referred to herein may have 2 from to 70 amino acid residues; and in other embodiments, they may have from 2 to 50 amino acid residues. In other embodiments, proteins or polypeptides or peptides referred to herein may have from a few tens of amino acid residues, e.g. 20, to up to a thousand or more amino acid residues, e.g. 1200. In still other embodiments, proteins, polypeptides, peptides, or fragments thereof, may have from 10 to 1000 amino acid residues; or they may have from 20 to 500 amino acid residues; or they may have from 20 to 200 amino acid residues.

"Polymer" means a plurality of monomers connected into a linear chain. Usually, polymers comprise more than one type of monomer, for example, as a polynucleotide comprising A's, C's, G's and T's, or a polypeptide comprising more than one kind of amino acid. Monomers may include without limitation nucleosides and derivatives or analogs thereof and amino acids and derivatives and analogs thereof. In some embodiments, polymers are polynucleotides, whereby nucleoside monomers are connected by phosphodiester linkages, or analogs thereof.

"Polynucleotide" or "oligonucleotide" are used interchangeably and each mean a linear polymer of nucleotide monomers. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Sequence determination", "sequencing" or "determining a nucleotide sequence" or like terms in reference to polynucleotides includes determination of partial as well as full sequence information of the polynucleotide. That is, the terms include sequences of subsets of the full set of four natural nucleotides, A, C, G and T, such as, for example, a sequence of just A's and C's of a target polynucleotide. That is, the terms include the determination of the identities, ordering, and locations of one, two, three or all of the four types of nucleotides within a target polynucleotide. In some embodiments, the terms include the determination of the identities, ordering, and locations of two, three or all of the four types of nucleotides within a target polynucleotide. In some embodiments sequence determination may be accomplished by identifying the ordering and locations of a single type of nucleotide, e.g. cytosines, within the target polynucleotide "catcgc . . . " so that its sequence is represented as a binary code, e.g. "100101 . . . " representing "c-(not c)(not c)c-(not c)-c . . . " and the like. In some embodiments, the terms may also include subsequences of a target polynucleotide that serve as a fingerprint for the target polynucleotide; that is, subsequences that uniquely identify a target polynucleotide, or a class of target polynucleotides, within a set of polynucleotides, e.g. all different RNA sequences expressed by a cell.

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

What is claimed is:

1. An apparatus for detecting sequences of optical signals from parallel reactions on an array, the apparatus comprising:
   an array of nanowells each comprising a reaction site and each capable of confining a reaction that generates a sequence of optical signals, the nanowells of the array being arranged in clusters each comprising a plurality of nanowells and each different cluster of nanowells being disposed within a different resolution limited area; and
   an optical system operatively associated with the array for detecting optical signals from the reactions.

2. The apparatus of claim 1 wherein said clusters are arranged in a rectilinear array or in a hexagonal array.

3. The apparatus of claim 2 wherein said nanowells each comprise a zero mode waveguide.

4. The apparatus of claim 1 wherein said optical system is capable of distinguishing said clusters of said array containing a single said reaction generating a single sequence of optical signals from said clusters containing more than one said reaction generating more than one sequence of optical signals.

5. A method of sequencing a plurality of nucleic acid molecules, the method comprising the steps of:
   (a) providing an apparatus comprising an array of nanowells each comprising a reaction site and each capable of confining a reaction that generates a sequence of optical signals, the nanowells of the array being arranged in clusters each comprising a plurality of nanowells and each different cluster of nanowells being disposed within a different resolution limited area; and
   an optical system operatively associated with the array for detecting optical signals from the reactions;
   (b) mixing in the nanowells of the array a plurality of target nucleic acid molecules, primers complementary to the target nucleic acid molecules, polymerization enzymes, and more than one type of nucleotides or nucleotide analogs with distinct optical labels to be incorporated into a plurality of nascent nucleotide strands, each strand complementary to a respective target nucleic acid molecule;
   (c) subjecting the mixture of step (b) to a polymerization reaction under conditions suitable for formation of the nascent nucleotide strands by template-directed polymerization of the nucleotides or nucleotide analogs, which generate a sequence of optical signals upon illumination with an incident light beam; and
   (d) identifying the nucleotides or the nucleotide analogs incorporated into the nascent nucleotide strands from the sequences of optical signals detected by the optical system.

6. The apparatus of claim 5 wherein said clusters are arranged in a rectilinear array or in a hexagonal array.

7. The method of claim 6 wherein said nanowells each comprise a zero mode waveguide.

8. The method of claim 5 wherein said optical system distinguishes said clusters of said array containing a single said polymerization reaction generating a single sequence of optical signals from said clusters containing more than one said polymerization reaction generating more than one sequence of optical signals.

* * * * *